(12) United States Patent
Rahimi

(10) Patent No.: US 9,192,453 B2
(45) Date of Patent: Nov. 24, 2015

(54) DYNAMIC BRACKET SYSTEM

(71) Applicant: Hessam Rahimi, Dallas, TX (US)

(72) Inventor: Hessam Rahimi, Dallas, TX (US)

( * ) Notice: Subject to any disclaimer, the term of this patent is extended or adjusted under 35 U.S.C. 154(b) by 0 days.

(21) Appl. No.: 14/014,328

(22) Filed: Aug. 29, 2013

(65) Prior Publication Data

US 2014/0065568 A1    Mar. 6, 2014

Related U.S. Application Data

(63) Continuation-in-part of application No. 13/598,931, filed on Aug. 30, 2012.

(60) Provisional application No. 61/819,536, filed on May 4, 2013.

(51) Int. Cl.
*A61C 7/14*     (2006.01)
*A61C 7/16*     (2006.01)
*A61C 7/20*     (2006.01)

(52) U.S. Cl.
CPC . *A61C 7/146* (2013.01); *A61C 7/14* (2013.01); *A61C 7/141* (2013.01); *A61C 7/16* (2013.01); *A61C 7/20* (2013.01)

(58) Field of Classification Search
CPC .................................. A61C 7/14; A61C 7/141
USPC ....................................................... 433/16, 8
See application file for complete search history.

(56) References Cited

U.S. PATENT DOCUMENTS

| 3,421,221 A | | 1/1969 | Silverman et al. | |
|---|---|---|---|---|
| 3,423,833 A | * | 1/1969 | Pearlman | 433/16 |
| 3,461,559 A | | 8/1969 | Silverman | |
| 3,721,005 A | * | 3/1973 | Cohen | 433/16 |
| 3,946,488 A | | 3/1976 | Miller et al. | |
| 4,139,945 A | | 2/1979 | DiGiulio | |
| 4,186,488 A | | 2/1980 | Wallshein | |

(Continued)

FOREIGN PATENT DOCUMENTS

WO    WO2008/119119 A1    10/2008
WO    WO2008/142690 A2    11/2008

OTHER PUBLICATIONS

Online Encyclopedia—Shape-memory alloy (downloaded on Jul. 2, 2013); http://en.wikipedia.org/wiki/Shape-memory_alloy.

(Continued)

*Primary Examiner* — Ralph Lewis
(74) *Attorney, Agent, or Firm* — Antoinette G. Giugliano; AGG Intellectual Property Law

(57) ABSTRACT

This invention is a dynamic orthodontic bracket system which allows brackets to be adjusted for particular angulations required for each individual tooth of a patient, while the frames are continuously attached to tooth surface. The orthodontist manually adjusts the relationship of a bracket and a frame during treatment eliminating the necessity of a full repositioning of all components. The bracket is positioned such that it can move in various directions to achieve a proper angulation for tooth repositioning. The base of the bracket and the interior surface of the frame can be textured to provide friction and secure the components once positioned for proper tooth movement. The exterior of the frame can also be textured to provide more secure attachment to the surface of the tooth. This system will lead to lower treatment cost and quicker adjustments of the orthodontic bracket system.

25 Claims, 15 Drawing Sheets

(56) References Cited

U.S. PATENT DOCUMENTS

| | | | |
|---|---|---|---|
| 4,243,387 A * | 1/1981 | Prins | 433/16 |
| 4,487,581 A | 12/1984 | Adler | |
| 4,597,739 A | 7/1986 | Rosenberg | |
| 5,954,502 A | 9/1999 | Tuenge et al. | |
| 7,306,458 B1 * | 12/2007 | Lu | 433/16 |
| 7,431,586 B1 * | 10/2008 | Silverman | 433/9 |
| 7,597,553 B2 | 10/2009 | Kimura | |
| 7,819,660 B2 | 10/2010 | Cosse | |
| 7,963,767 B2 | 6/2011 | Lewis et al. | |
| 8,038,438 B2 | 10/2011 | Ruiz Diaz et al. | |
| 8,459,988 B2 | 6/2013 | Dumas | |
| 8,550,814 B1 | 10/2013 | Collins | |
| 2005/0136369 A1 | 6/2005 | Rosenberg | |
| 2007/0128571 A1 | 6/2007 | Kimura | |
| 2007/0259302 A1 | 11/2007 | Jayawardena | |
| 2008/0293005 A1 * | 11/2008 | Rahlis et al. | 433/16 |
| 2011/0300502 A1 | 12/2011 | Kishi | |
| 2012/0225398 A1 | 9/2012 | Fallah | |
| 2013/0078595 A1 | 3/2013 | Solano Reina et al. | |

OTHER PUBLICATIONS

Online Encyclopedia—Shape-memory polymer (downloaded on Jul. 2, 2013); http://en.wikipedia.org/wiki/Shape-memory_polymer.

Reinventing the Science of Braces (downloaded on May 7, 2012); http://www.suresmile.com.

Online Encyclopedia—Suresmile (downloaded on May 7, 2012); http://en.wikipedia.org/wiki/Suresmile.

Online Encyclopedia—Self ligating braces (downloaded on Jun. 18, 2012); http://en.wikipedia.org/wiki/Self-ligating_braces.

Online Encyclopedia—Dental braces (downloaded on May 7, 2012); http://en.wikipedia.org/wiki/Dental_braces.

Dental Braces and Retainers: Types, Care, What to Expect (downloaded on May 7, 2012); http://www.webmd.com/oral-health/guide/braces-and-retainers.

* cited by examiner

DYNAMIC BRACKET SYSTEM

RELATED APPLICATION

This application claims the benefit of U.S. Provisional Application No. 61/819,536, filed May 4, 2013, and is a continuation-in-part of U.S. application Ser. No. 13/598,931, filed Aug. 30, 2012.

The entire teachings of the above applications are incorporated herein by reference.

BACKGROUND OF THE INVENTION

Orthodontics is a specialty in dentistry that moves teeth within the jaw bone and straightens the teeth by moving them to the proper three-dimensional location. In orthodontics, brackets are pieces of metal with a slot that accepts a flexible or rigid metallic wire. Such brackets are conventionally bonded to the teeth on a base (via a frame) and serve as vehicles allowing the orthodontist to apply force to the tooth to move it across the wire to its proper location with the proper angulation.

The interaction of force, wires and brackets guides the three dimensional movement of the tooth. The force applied to the teeth, by the wire, forces the teeth to slowly alter their positions to align with the wire and therefore position them correctly in three dimensions.

Conventional brackets generally have a fixed slot wherein the position of the slot relative to the tooth is fixed. Historically, brackets were the same for all teeth, regardless of patient individuality. Since every tooth has a unique three dimensional relationship with the rest of the teeth, the orthodontist was required to bend the wire that passed across the bracket slot in order to correct tooth angulation for each individual tooth.

In orthodontics, the angulation of the bracket slot in each dimension is described differently. The angulation of the bracket slot in the left-right direction is called 'tip' and the angulation of slot in the back-forward direction is called 'torque'. An average tip and torque has been calculated for every tooth, based on studies of normal dentitions. A modification was presented a few decades ago by which specific brackets were created for every tooth according to their average angulations so that when a straight wire was passed through the slot, the difference between the angle of the straight wire and the angle of the slot would force the tooth to track the wire and achieve the proper angulation. However, the inaccuracies occurred when a bracket was not bonded to the proper location on the tooth, which led to an improper angulation of the tooth and ultimately to a misaligned tooth.

Also, the presumed angulations are merely averages, based on estimates of average sizes and shapes of teeth. Each individual is different with varying morphology for their teeth. Whenever a patient's teeth do not fall within the normal range, the straight wire technique does not produce optimum tooth angulation and location. Commonly, brackets are not always placed in the proper location on the tooth resulting in erroneous bracket positioning. In order to correct for such problems, a certain number of brackets are repositioned during the course of the treatment to address these inaccuracies and improper bracket placements. Repositioning is both time-consuming and expensive and oftentimes does not cure the improperly positioned bracket. The process of bracket repositioning involves a patient's office visit, removal of the old bracket, polishing of the tooth surface, priming of the surface and application of the new bracket to the surface. This process can take anything from 5 to 15 minutes per tooth, depending on the location of the bracket and the experience of the clinician.

A need exists for a dynamic bracket system that allows the clinician to change the angulation of the bracket to achieve proper tooth alignment. A further need exists for a dynamic bracket system that allows a change in angulation in a number of different directions. Yet a further need exist to do so using a system that is efficient, easy to adjust and cost effective.

SUMMARY OF THE INVENTION

The dynamic bracket system of the present invention is designed to equip the practitioner with the ability to conveniently modify the position, tip and torque of the bracket slot component during the course of treatment, without having to remove and rebond the bracket. The dynamic bracket system of the present invention increases efficiency and quality of patient care. A dynamic bracket system of the present invention includes a frame, bracket slot component, stationary cover, and a moving cover. The frame, with its textured bottom side, can be bonded to the tooth surface with an adhesive material. The bracket slot component (also referred to as the "bracket") includes a base, a stem (also referred to as a "neck") and the top portion of the bracket, which includes an upper arm, a slot, and a lower arm. In some embodiments, instead of upper arm and lower arm designations, the terms arm A, arm B, arm C, and arm D are used.

In an embodiment, the bracket system uses friction to secure the slot component after it is repositioned. Within the bracket system, the stem, immediately below the top portion of the bracket, can be positioned within the bracket compartment opening, between the junction of the moving cover and stationary cover. In some embodiments, instead of a moving cover and a stationary cover, there is one receiving member that is part of a single piece frame. The bracket base can be secured by vertical pressure from the joining of the moving cover and stationary cover within the frame. The base of the bracket slot component, below the stem, can rest above the textured interior of the bracket frame. The textured interior surface ensures that the bracket component does not move freely within the space created between bracket frame and the covers, or between the groove created between the receiving member and the anchoring member. The diameter of the bracket stem is smaller than the opening created by the covers such that the bracket stem fits within the opening. The base of the bracket slot component can be wider than the stem yet narrower than the frame.

The dynamic bracket system, in an embodiment, also includes a stationary cover and a moving cover which slide into position within the bracket frame along guiding grooves in the interior side walls of the bracket frame. The guiding groove is an indentation that runs along the top interior edge of the frame. The ends of the stationary cover and moving cover are tapered to allow sliding of the moving cover over the stationary cover in the guiding groove. The horizontal force on the covers as the covers move towards the end of the grooves, sliding friction of the covers over one another, as well as vertical pressure on the base of the bracket combine to limit the movement of the covers.

Each cover, in an embodiment that has such covers, has depressions at the exterior edge of the cover, which lock onto projections along the guiding groove of the frame. In this embodiment, the stationary cover and moving cover both have irregularly shaped interior edges. When the stationary and moving covers are in position within the bracket frame, an opening to the bracket slot compartment is created at the junction of the interior edge of the two covers. During initial assembly of the bracket, first, the stationary cover is guided into position within the bracket frame, along the guiding grooves. The stationary cover is locked into place when the depression on the stationary cover connects with the projection along guiding groove.

The bracket slot component is inserted into the space between the cover and the frame so that the base of the slot component lies beneath the cover and the rest of the slot component lies above it. Finally, the moving cover is guided into position within the bracket frame until the depressions connect with the projections of the guiding groove. The bracket slot component is secured between the frame and the covers by the secure connection between the stationary cover and the moving cover. The covers are locked together by a locking mechanism such as ball and socket, key and key hole or force of friction. The guiding grooves are slightly wider than the width of the covers so that when the two covers come together, the stationary cover is pushed down as the moving cover is wedged between a side of the guiding groove and the stationary cover. Without the slightly wider guiding grooves, a positive pressure or force of friction could be more difficult to create so as to secure the covers.

This design allows for the bracket slot component to be adjusted within the confines defined by the stationary cover and moving cover when the moving cover is in the 'open' configuration and not fixed in place. The bracket slot component locks in place when the moving cover is in the 'lock' configuration. The slot component is able to rotate 360 degrees as well as move within the range defined by the difference in radius of the stem and the opening to the bracket compartment (also referred to as the inner borders of the covers). The frame's exterior or tooth-side surface can be textured to increase bond strength. The tooth-side surface of the bracket frame can have adaptive curves associated with the morphology of tooth surface. The base of the stem and the base-side of the frame can have micro-depressions to prevent sliding of the slot when the moving cover is in lock position. This bracket system uses friction as a means to prevent alteration of position of bracket slot relative to the frame.

The two covers have a locking mechanism when they meet that prevents the moving cover from opening unless subjected to horizontal force applied through a regular orthodontic plier to its opening ledge. When the two cover extensions meet, a positive downward pressure or force of friction is applied on the base of the slot component, locking it in place. This increased positive pressure is created as the sloped surface of the moving cover extension slides above the sloped surface of the stationary cover extension. The moving cover is held in place by the guiding grooves or narrow cut outs made in the inner surface of the walls of the base frame, allowing it to move back and forth in the horizontal direction. When the stationary cover is positioned in the frame wall's guiding groove, it will lock in place when pushed to the edge of the frame and the opposing socket in the stationary cover. The moving cover is locked in place when engaged with the stationary cover. The stationary cover and the moving cover are secured when the depressions on these covers are positioned within the projections in the guiding groove, at the exterior edge of the frame. The frame wall surrounds the bracket frame except the feeding wall where it allows for the base of the bracket compartment to slide underneath the covers. The moving cover has a notch close to the edge on the feeding side of the frame that prevents it from coming loose when the moving cover is open unless subjected to sufficient force from a human hand using a dental plier or other tool. When subjected to sufficient force, practitioner can replace the moving cover in cases where breakage happens or the practitioner is required to modify the slot configuration for any reason, whether it is damaged or a different torque number is required.

The designs detailed above are some of the basic embodiments described herein that make use of covers. In addition to these, certain embodiments that do not need separate covers, and that can instead use integral parts of the frame itself, are also encompassed by the present invention.

In an aspect, the present invention includes a bracket system for use as part of orthodontic braces. The bracket system has a frame and a bracket, in which the frame can be adjusted so that the bracket can be inserted into it, removed from it, and locked into it. Additionally, in some embodiments, the bracket comprises a base, a neck, and one or more arms. The base of the bracket is received by the frame, in part or in full, and the one or more arms can create a slot that can receive a wire. In some embodiments, the exterior surface of the frame is textured so that it ensures that the friction between the tooth and the frame is high enough to prevent sliding. In other embodiments, the interior surface of the frame can be textured too, in addition to the bottom surface of the base. Such texturing can ensure that the lock between the bracket and the frame is stronger that what would have been achieved by the fastener, to be explained later, alone. In alternative embodiments, the bracket has four arms. These four arms can create two slots, for example.

In some embodiments, the bracket system has a frame that comprises an anchoring member to anchor the frame to a tooth, a receiving member to receive a bracket, a hinge that connects the two members mentioned, an opening in the receiving member to accept a bracket, and a fastener to lock the relative positions of the receiving and anchoring members. In certain embodiments, the bracket within the frame can rotate around 360 degrees and it can also move in any direction along the 360 degrees.

In a particular embodiment, the fastener of the bracket is a clip that exists as part of the single-piece forming the frame. The clip can have a stopper to stop a potentially dislocating receiving member. The clip can also have teeth that can align with teeth on the receiving member. The bracket system, in any of the embodiments, can be decorated with markings, either orthogonal to any of the sides or oblique to any of the sides, to facilitate alignment of the bracket and the frame with respect to each other. The markings can exist on both the bracket and the frame.

In another aspect, an embodiment includes one or more screws as part of the fastener. The screws can be received by one or more screw receivers on the receiving member as well as on the anchoring member. The screw receivers on the anchoring member need not allow full passage of the screws; or if they do, they can be used in conjunction with screws that are designed with a specific length. In a separate embodiment, the fastener can be manufactured in the form of a lever. The lever can have a lever handle and a lever lock. The lever lock, when the handle is moved, can ensure that the receiving member and the anchoring member are tightly locked when a bracket is in place.

In various embodiments, one or more components of the bracket system can be made, in part or in whole, from materials such as nickel-titanium alloys, titanium-molybdenum alloys, and/or stainless steel. The frame, in some embodiments, can be placed onto the facial (labial or buccal) side of a tooth, whereas, in others, it can be placed onto the lingual side of a tooth. In some embodiments, the brackets are self-ligating brackets or can be adapted to be self-ligating.

In alternative embodiments, methods of using a bracket system are disclosed. One method includes the steps of anchoring the frame of a bracket system onto a tooth, placing a bracket into the frame, and fastening the frame to lock the bracket in place. Alternatively, the method of the present invention can include the steps of placing a bracket into a frame that has been anchored onto a tooth, and fastening the frame to lock the bracket in place. Various embodiments of such methods of using a bracket system can be modified in accordance with the embodiments of the bracket system disclosed herein.

Additionally disclosed are kits that have a frame and a bracket. The kits can have as frames and brackets, any of the embodiments disclosed herein. The kits can also include wires (e.g., archwires), ligating members, or other tools to facilitate the use of the bracket systems.

The present invention has several advantages. Because the frame can be manufactured as a single piece, production costs are lower, and also the potential of a piece being lost is lower. The simplicity of a single piece also facilitates the ease of using the bracket system. The combined locking action of the fasteners and the textured surfaces ensures that the bracket and the frame do not move relative to each other unless desired. The ability to rotate the bracket 360 degrees, and also the ability to move (e.g., translate) the bracket in any direction along the mentioned 360 degrees enables a clinician to achieve any desired orientation of the bracket to bring about a needed orthodontic adjustment of a tooth. The obviated need to remove the bond between a tooth and a bracket during treatment, because of the use of a frame separate from the bracket, facilitates faster treatment times and reduces any potential of damaging the tooth due to such unbonding-rebonding cycles.

BRIEF DESCRIPTION OF THE DRAWINGS

The foregoing and other objects, features, and advantages of the invention will be apparent from the following more particular description of preferred embodiments of the invention, as illustrated in the accompanying drawings in which parts are referred to by reference characters across views. The drawings are not necessarily to scale, emphasis instead being placed on illustrating the principles of the invention.

The bracket system in the figure is seen in an unlocked position due to the lever being in a raised position.

DETAILED DESCRIPTION OF THE INVENTION

A description of preferred embodiments of the invention follows.

Figure 1:
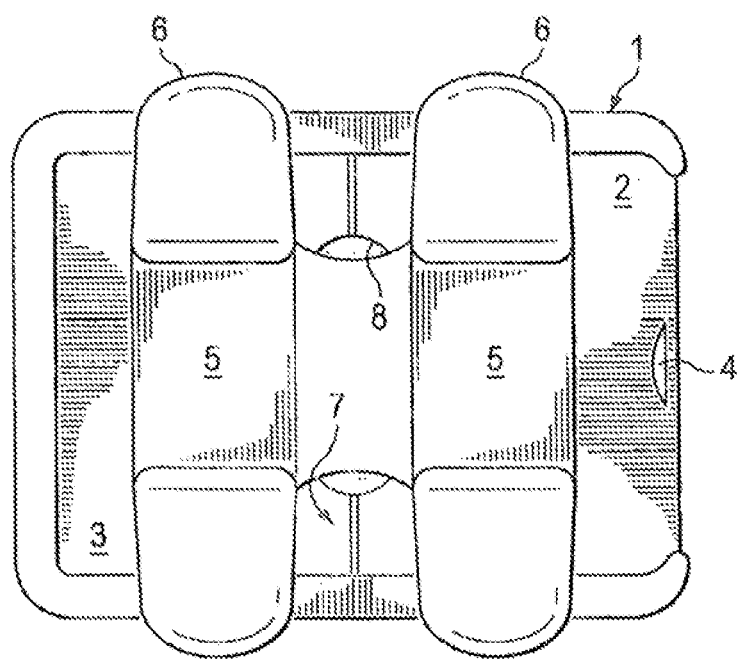
FIG. 1 is a top view of a dynamic bracket system, where Ref. 1 is the bracket system frame, Ref. 2 is the moving cover, Ref. 3 is the stationary cover, Ref. 4 is the releasing notch, Ref. 5 is the bracket wire slot, Ref. 6 is a bracket slot component, Ref. 7 is the junction between the moving and stationary covers, and Ref. 8 is the opening to the bracket compartment

FIG. 1 is a top view of an embodiment of the dynamic bracket system. The shown dynamic bracket system is composed of a bracket system frame (1) which is connected to the tooth surface (9) (not shown in FIG. 1 but shown in FIG. 2). The interior of the shown frame has grooves or guiding lines (17) for the insertion of the stationary cover and moving cover. See FIG. 4. The moving cover (2) is inserted after the stationary cover (3) into the frame such that the covers connect at a junction (7). The connected covers exert a vertical pressure on the bracket base (10) that helps secure the base inside the bracket compartment (16). The moving cover (2) has a releasing notch (4) into which an orthodontic plier or tool can be inserted in order to release the moving cover from the frame (1). Once the stationary cover (3) is in place within the frame, the bracket slot component (6) is inserted followed by another bracket slot component (6). Each bracket slot component, in this embodiment, has a bracket wire slot (5) for the insertion of a guiding wire into the bracket system. The interior edges of both the stationary cover and the moving cover contain a cutout section such that an opening to the bracket compartment (8) is created where the bracket slot component (6) will be inserted within the bracket system.

Figure 2:
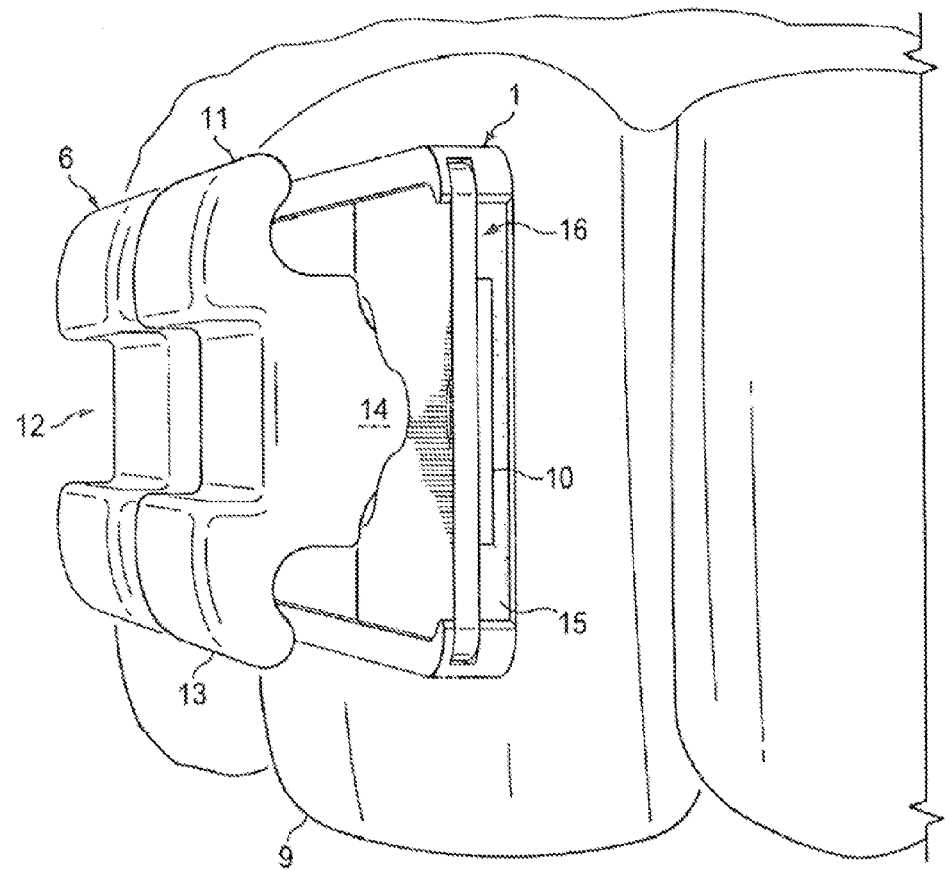
FIG. 2 is a perspective view of a dynamic bracket system, where Ref. 1 is the bracket system frame, Ref. 6 is the bracket slot component, Ref. 9 is the tooth surface, Ref. 10 is the bracket base, Ref. 11 is the upper arm of the bracket slot component, Ref. 12 is the wire slot of the bracket slot component, Ref. 13 is the lower arm of the bracket slot component, Ref. 14 is the bracket stem, and Ref. 16 is the bracket slot compartment

FIG. 2 is a perspective view of the dynamic bracket system that was shown in FIG. 1. The bracket system can be attached to the front surface of the user's tooth (9). The bracket slot component (6) is composed of an upper arm (11), a wire slot (12), a lower arm (13), a stem (14) and a base (10). The bracket slot component (6), in this embodiment, is inserted into the frame (1) between the stationary cover and moving cover. The bracket base (10) of the bracket slot component rests beneath the stationary and moving covers in the bracket slot compartment (16), where the bracket base is secured by vertical pressure from the covers. The interior surface of the bracket slot compartment, in this embodiment, is textured (15) to prevent movement of the bracket slot component (6). The bracket stem (14) is inside the opening (8) for the bracket slot compartment (16). The opening (8) is created, in this embodiment, by the joining of the edges of the stationary cover and moving cover. See FIG. 3. Each cover has an irregularly shaped interior edge, which creates an opening to the compartment (8) to allow for the insertion of the bracket stem between the joined covers.

Figure 3:
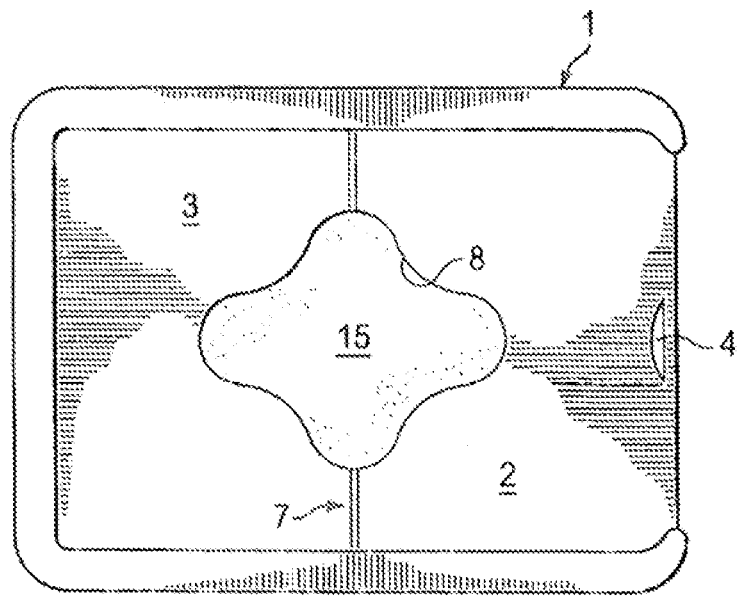
FIG. 3 is a top view of a bracket slot compartment opening created by joining of stationary and moving covers, where Ref. 1 is the bracket system frame, Ref. 2 is the moving cover, Ref. 3 is the stationary cover, Ref. 4 is the releasing notch, Ref. 7 is the junction between the moving and stationary covers, and Ref. 8 is the opening for the bracket slot compartment

FIG. 3 is a top view of the bracket slot compartment opening created by the joining of the stationary and moving covers, corresponding to parts of the embodiment shown in FIG. 1 and FIG. 2. The stationary and moving covers each contain an irregularly shaped interior edge that creates an opening (8) for the bracket slot compartment when the covers are aligned. The stationary cover (3) is inserted into the bracket system frame (1) along the guiding grooves (17). Then the moving cover (2) is also inserted along the guiding grooves (17) until its sloped edge meets the sloped edge of the stationary cover (3) at the junction point (7). The outer edge of the moving cover (4) has a releasing notch (4) that assists in the removal of the moving cover. Pressure applied to the releasing notch with a dental tool will release the moving cover from its position. The dental tool can be any type of the following: cutter, explorer, plier, stripper, or scaler. The opening (8) to the bracket slot component is created by the joining of the stationary and moving covers at their interior edges.

Figure 4:
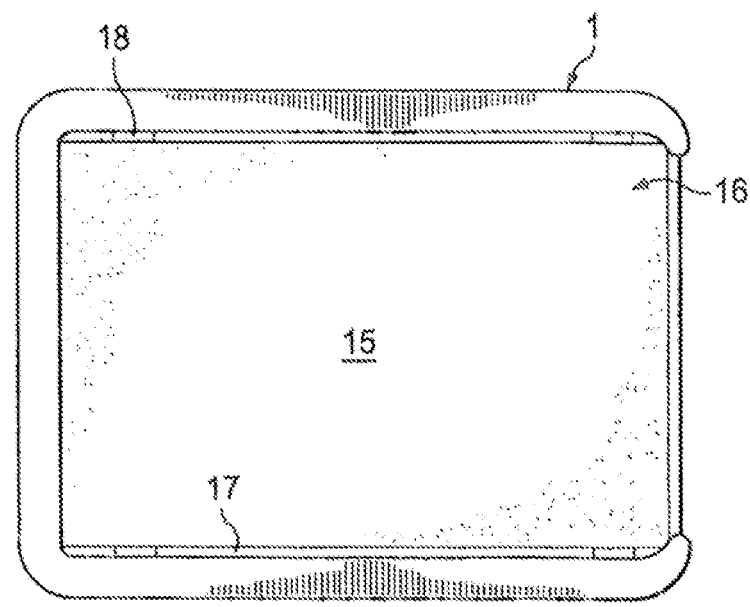
FIG. 4 is a top view of a bracket slot compartment without covers, where Ref. 1 is the bracket frame, Ref. 15 is the textured surface of the interior of the bracket slot compartment, Ref. 16 is the bracket compartment, and Ref. 17 is the guiding grooves within the interior of the frame

FIG. 4 is a top view of the bracket slot compartment (16) without the stationary cover or moving cover. The embodiment shown in this figure, and described in this paragraph, corresponds to the ones shown in FIG. 1, FIG. 2, and FIG. 3. The components of the bracket system are assembled within the bracket frame (1). The interior edges of the frame, in this embodiment, have guiding grooves (17) that the stationary and moving covers glide along as the covers are inserted into the frame. The interior surface of the bracket compartment is textured (15) to prevent movement of the bracket base (10) within the compartment (16).

Figure 5:
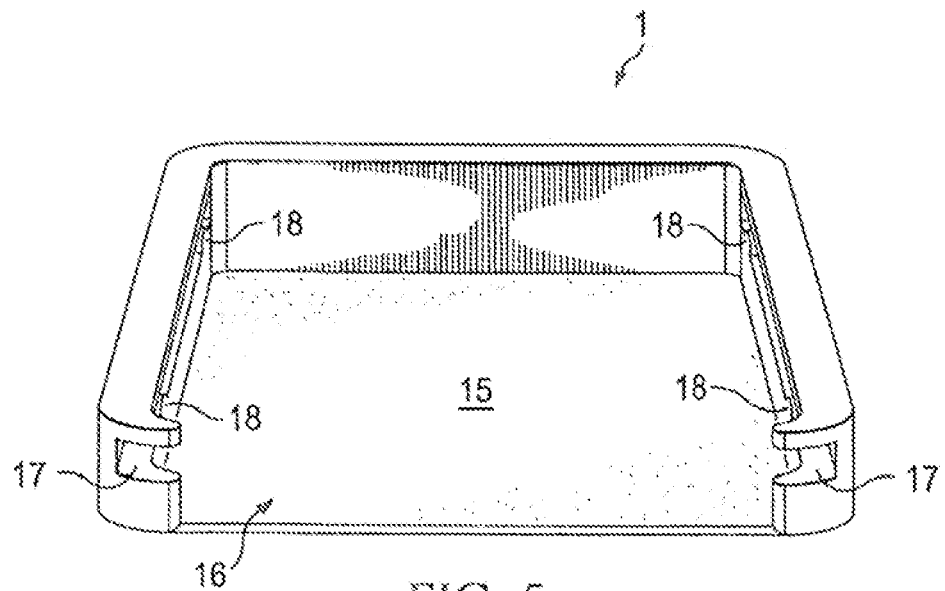
FIG. 5 is a perspective view of a bracket slot compartment without covers, where Ref. 1 is the bracket frame, Ref. 15 is the textured surface of the interior of the bracket slot compartment, Ref. 16 is the bracket compartment, Ref. 17 is the guiding grooves within the interior of the frame, and Ref. 18 is a projection along the guiding groove

FIG. 5 is a perspective view of the bracket slot compartment (16) without the stationary cover or moving cover. The embodiment shown in this figure, and described in this paragraph, corresponds to the one shown in FIG. 1 through FIG. 4. The components of the bracket system are assembled within the bracket frame (1). The interior edges of the frame (1) have guiding grooves (17) that the stationary and moving covers glide along as the covers are inserted into the frame (1). There are a number of projections (18), along the surface of the guiding grooves (17) that lock with the depressions (19) on the moving and stationary covers to secure the covers to the frame (1). The connection between the projections (18) and the depressions (19) also exerts vertical pressure on the bracket base (10) within the bracket compartment (16). The interior surface of the bracket compartment (16) is textured (15) to prevent movement of the bracket base within the compartment (16).

Figure 6:
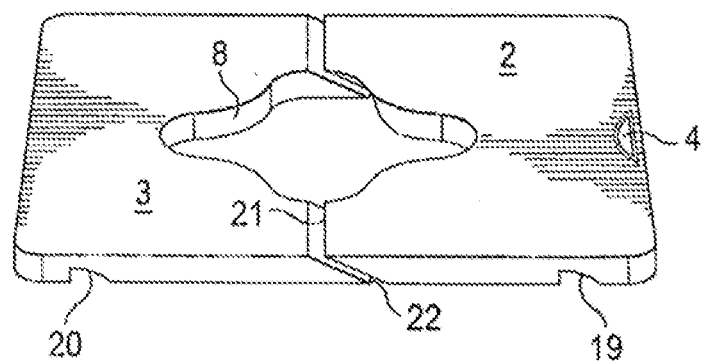
FIG. 6 is a perspective view of a stationary cover and moving cover in an unlocked position, where Ref. 2 is the moving cover, Ref. 3 is the stationary cover, Ref. 4 is the releasing notch, Ref. 8 is the opening for the bracket slot compartment created by the joining of the moving and stationary covers, Ref. 19 is the securing depression on the moving cover, Ref. 20 is the securing depression on the stationary cover, Ref. 21 is the connecting edge of the moving cover, and Ref. 22 is the connecting edge of the stationary cover

FIG. 6 is a perspective view of the stationary cover and moving cover in an unlocked position. The moving cover (2) and the stationary cover (3) both have connecting edges (21, 22) that lock together at the junction. In addition, the moving cover (2) and the stationary cover (3) both have cutout sections on the interior edges of the covers. When the moving cover and the stationary cover are locked or joined, a closed off round opening (8) is created. The bracket component can be positioned within this opening (8) to the bracket slot compartment (16) when the bracket system is fully assembled. The moving cover has dual securing depressions (19) at its exterior edges that serve to secure the moving cover (2) and prevent the cover from falling out of the frame (1). These depressions (19) connect with projections (18) along the guiding groove (17) to secure the cover in the frame. The stationary cover also has dual securing depressions (20) at its outer edges that serve to secure the stationary cover (3) and prevent the cover from falling out of the frame. The securing depressions on the bottom side of the covers protrude and prevent the covers from sliding out of position. These depressions (20) connect with projections (18) along the guiding groove (17) to secure the cover in the frame (1). There is also a releasing notch (4) that unlocks the cover once an orthodontic plier is inserted in the latch with sufficient force from a hand or a dental tool.

Figure 7:
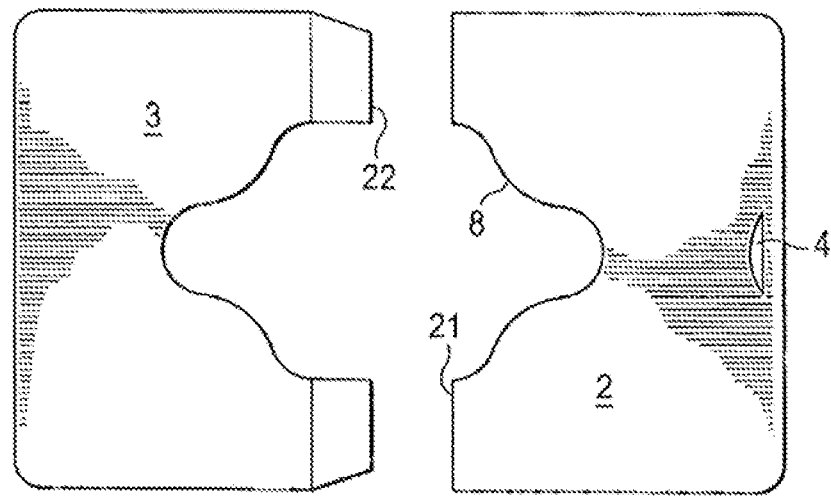
FIG. 7 is a close-up top view of covers in an unlocked position, where Ref. 2 is the moving cover, Ref. 3 is the stationary cover, Ref. 4 is the releasing notch, Ref. 8 is the opening for the bracket slot compartment created by the joining of the moving and stationary covers, Ref. 21 is the connecting edge of the moving cover, and Ref. 22 is the connecting edge of the stationary cover

FIG. 7 is a close-up top view of the covers in an unlocked position. The moving cover (2) and the stationary cover (3) both have connecting edges (21, 22) that lock together at the junction and cutout sections on the interior edges of both covers. When the moving cover and the stationary cover are locked or joined, a closed off round opening (8) is created. The moving cover has dual depressions (19) at its outer edges that serve to secure the moving cover and prevent the cover from falling out of the frame. The stationary cover also has dual securing depressions (20) at its outer edges that serve to secure the stationary cover (3) and prevent the cover from falling out of the frame. There is also a releasing notch (4) that unlocks the cover once an orthodontic plier is inserted in the latch with sufficient force from a hand or a dental tool.

Figure 8:
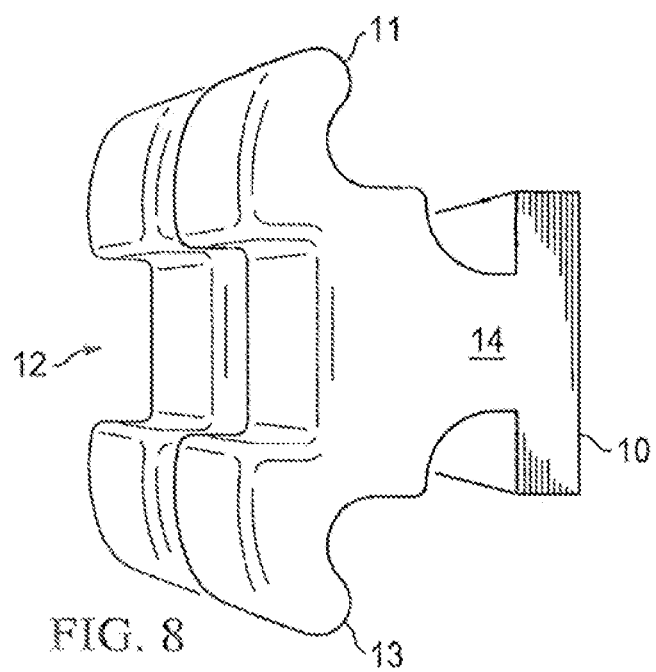
FIG. 8 is a perspective view of a bracket slot component, where Ref. 10 is the base of the bracket, Ref. 11 is upper arm of the bracket slot component, Ref. 12 is the slot of the bracket where the orthodontic wire is inserted, Ref. 13 is the lower arm of the bracket component, and Ref. 14 is the stem of the bracket

FIG. 8 is a side view of a bracket component. The shown bracket slot component is made of an upper arm (11) and a lower arm (13) with a slot (12) between the arms wherein an orthodontic wire would be inserted to aid in the movement of teeth. Two bracket slot components would collectively have two upper arms, two lower arms, and a slot that would run along both of the individual slots. Beneath the slot (13), lies the stem (14) of the bracket slot component. The stem is of a smaller diameter than the distance between the outside edges of the upper and lower arms of the bracket component. Beneath the stem, lies the base of the bracket (10) which is of a length larger than that of the stem. The stem (14) of the bracket slot component is inserted through the bracket compartment opening (8) and the base (10) of the bracket slot component rests against the textured interior surface (15) of the bracket compartment in the bracket frame (1).

The embodiments described herein can be used to create mesial movements (toward the central teeth), distal movements (toward the last molars), lingual movements (toward the tongue behind the teeth), facial movements (toward the lips (labial) or toward the cheeks (buccal)), apical movements (toward the root), coronal movements (toward the crown), or any combination thereof. Certain embodiments are especially suited for mesial, distal, lingual, and facial movements. Other terms for the types of movements that can be created include tipping, torqueing, translation, root uprighting, rotation, extrusion, and intrusion. Tipping refers to a type of mesiodistal movement, and torqueing is a buccolingual movement. Extrusion is a coronal, and intrusion an apical movement. Forces required for these types of movements can be in the 15 to 150 g range or higher, and are attainable with the embodiments disclosed herein. The units used herein for forces are grams, abbreviated as "g". Even though gram, from a physical standpoint is a unit for mass, in orthodontics, it is sometimes used as a shorthand for gram-force, and is understood to stand for the amount of force the standard gravity (e.g., 9.8 m/s$^2$) would exert on an object having a certain mass. By this definition used herein, 1 g would be equivalent to a force of approximately 0.0098 N (Newton), while 1N would approximately equal 101.97 g. In some publications, it is possible to come across different definitions of some of the terms relating to the movements of teeth. For example, tipping is sometimes referred to as the simplest orthodontic movement that occurs at about the center of resistance of a tooth (sometimes described as ⅓ from root apex or 40% of root length from alveolar crest). For such a tipping, forces are high at apex and alveolar crest, for example 35-70 g, while they reduce to zero at center. Such a broad definition (not used herein) would combine the definitions of tipping (as used herein) and torqueing (as used herein) into one general term. Translation can be referred to as any bodily movement where all of periodontal ligament is uniformly loaded with forces such as 70-150 g. Rotation is sometimes believed to need a level of force that is theoretically high, and because of the ensuing compression of the periodontal ligament with forces around 35-100 g, tipping may accompany an attempted rotation. Extrusion, as a vertical movement, depends on creating tension at the fibers of periodontal ligament, of around 35-60 g. Intrusion, a similarly vertical movement, has forces of 10-25 g concentrated at root apex. Forces used to bring different tooth movements about can be applied continuously (at a light level, sometimes referred to as "ideal") or only when wearing an appliance (sometimes referred to as "interrupted"). As a hybrid of the two types above, the force can also be applied such that it gradually reduces (e.g., to zero) between visits to a clinician (this type of force is sometimes referred to as "intermittent"). The appliances used to apply forces can be, in general, fixed or removable.

From a purely physical standpoint, orthodontic tooth movements can be described as either translations, rotations, or a combination of the two. In some texts, it is possible to come across the term "tipping" to be used in the sense of a "combination" as described above (e.g., broadly as a combination of translation and rotation). A force that does not pass though the center of resistance of a tooth can cause the combination of translation and rotation, essentially resulting in movement with some rotational element. To create pure rotation, a single force is not enough; at least a couple (e.g., two forces) are needed.

Periodontal ligament (PDL) attaches a tooth to the alveolar bone and has fibroblasts, osteoblasts, osteoclasts, and undifferentiated cells, among others. PDL is at the interface between the tooth and the cortical bone. Cortical bone has slow turnover, whereas trabecular bone that is adjacent but further away from the tooth, has constant turnover. When force is applied to a tooth, PDL/bone receives the force and this leads to microfractures, in addition to other changes. Ultimately, osteoblasts mediate tension and osteoclasts mediate compression; hence, deposition (secretion of new bone by osteoblasts) and resorption (breaking down, by osteoclasts) of bone is accomplished. Level and duration of force are important for properly moving the teeth. For describing movements of the teeth, it is often useful to refer to the six different surfaces of a tooth. These surfaces are: gingival, occlusal, lingual, labial, mesial, and distal surfaces.

As mentioned, when a tooth moves, osteoblasts facilitate formation of new bone (e.g., bone deposition) from a location that a tooth has moved from, and osteoclasts facilitate removal (e.g., bone resorption) of bone tissue from the area that a tooth is moving into. The embodiments described herein can be used with a suitable pace of bracket adjustments so that bone formation and degradation are optimal, as determined by a clinician. In some embodiments, the used brackets can be made from translucent ceramic so that they are less visible against natural teeth. The brackets can be used with any wires, including nitinol (Nickel-Titanium alloy) wires with shape memory effects at various temperatures. Other materials for the wires include Titanium-Molybdenum alloys and stainless steel. The frames can be bonded to the teeth via bonding materials as well as via metal bands.

Brackets, wires, and other orthodontic supplies can be purchased from a variety of sources such as JesOrthopental, Fort Lauderdale, Fla.; Henry Schein Dental, Waltham, Mass.; and 3M Unitek Orthodontic Products, Monrovia, Calif.

One physical phenomenon on which some of the wires (e.g., archwires) used in contemporary bracket systems operate is shape memory effect, which allows application of appropriate forces to move the desired teeth. Some materials have the ability to return to a shape upon being exposed to a certain inducer, such as a change in temperature. Two common examples of such materials, sometimes called smart materials, are shape memory alloys (SMA) and shape memory polymers (SMP). SMAs can be set to a certain shape by being forged at a low temperature, and they will remember and try to return to that shape when they are placed at a higher temperature. For example, the desired shape can be set at a temperature that is much lower than the body's temperature, and the material, after being placed in or near a human body, would remember its original temperature and would try to return to it, in effect generating forces toward that original shape. These materials with shape memory can be used in the making of archwires for dental braces. The set and the postheating states are sometimes described as the martensitic and the austenitic states, respectively. Common alloys used to make SMAs include nickel-titanium and copper-aluminum-nickel alloys. While the most common SMAs remember their shape at a low temperature and try to return to it from a high temperature state, some SMAs can remember both a low and a high temperature state. The ability to create SMAs with varying materials and compositions of such materials allows the manufacturing of alloys of a wide variety of size and shape. While SMAs have been commonly employed for dental braces, SMPs may constitute a reasonable alternative in the future as well. SMPs can be induced to undergo transitions between states by changes in temperature, light, and fields such as electrical or magnetic ones. Some SMPs are also known to be able to remember three states, instead of only two (e.g., some can switch from a first state to a second one upon being subjected to a first inducer, and from the second one to a third one upon being subjected to a second inducer). Wires based on such elastic properties can be useful especially during the initial stages of treatment.

By frictional coefficient, it is referred to the ratio of a force opposing movement due to friction to a force pressing the objects toward each other. Sometimes also referred to as the coefficient of friction, the frictional coefficient is a measure of the friction, or of the force resisting the relative motion of two objects. For example, if the inner surface of the anchoring member of the frame and also the bottom surface of the bracket are made smooth, they would have a lower frictional coefficient compared to the case in which both are made with textured surfaces. The same can be said of the frictional coefficient between the external surface of the anchoring member of the frame and the surface of a tooth. By a high frictional coefficient, it is referred to a frictional coefficient that is high enough to prevent relative movements of the two objects (e.g., the bracket and the frame). By preventing the relative movements, what is meant is that the two objects would not move relative to each other more than a certain percentage of their average length during a certain period of time (e.g., 1%, 2%, 3%, 4%, 5%, or 10% within 1 day, 1 month, or 1 month). In the field, with respect to archwires and brackets, it is commonly believed that stainless steel can slide relatively well on stainless steel, whereas nickel-titanium alloy wires and ceramic brackets have higher frictional coefficients.

With the term single-piece, it is referred to an object (e.g., frame) that is not easily separated into components in a reversible way. Such an object may be made from substantially the same material throughout, or can be made from a mixture of materials. An object made of multiple objects welded together is also considered to be a single-piece object.

In some embodiments, self-ligating brackets can be used, in addition to more traditional brackets. Arch wires can be maxillary or mandibular, and they can be made of NiTi, TMA, or stainless steel. The wires can be parabolic shaped or shaped in any other way as desired. The wires can be straight wires, as opposed to requiring to be bent by a clinician. Retainers may need to be worn after the dental braces are removed. The brackets used can be modified to make them self-ligating brackets. Additional usable components include bands, molar tubes, brackets, buccal tubes, arch wires, and auxiliaries. Auxiliaries can include elastomeric products, coil springs, lingual arches, and extra-oral appliances.

The bracket system described herein can be positioned on the labial or buccal side (collectively, the facial side) of a tooth. In alternative embodiments, the bracket system can also be positioned on the lingual side.

In some embodiments, the terms "bracket" instead of "bracket slot component", "neck" instead of "stem", "interior surface" instead of "textured surface of interior", "arm A/B/C/D" instead of "lower/upper arm", and "groove" instead of "bracket compartment" are used.

Figure 9:
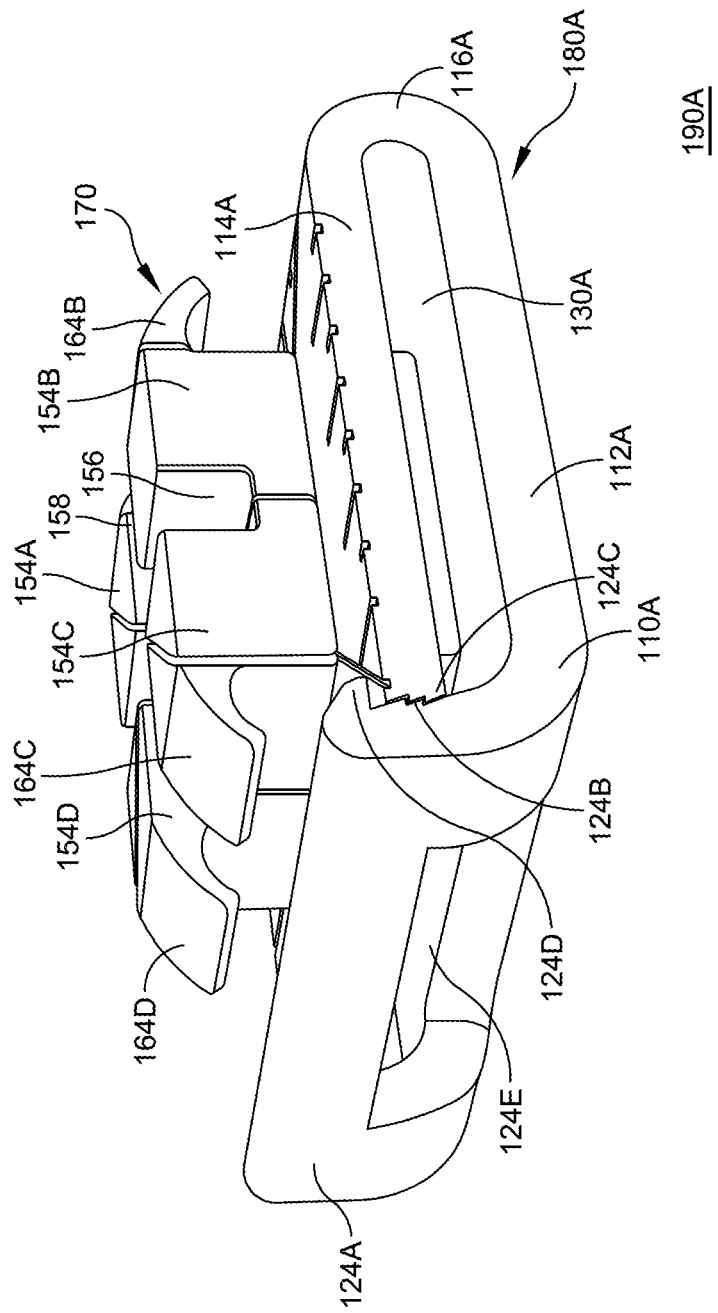
FIG. 9 is a schematic of a perspective view of an embodiment of the bracket system.

Referring to FIG. 9, another embodiment of the bracket system is shown. Bracket system 190A is shown in a perspective view with two of its parts: bracket 170 and frame 180A. Bracket 170 has arm 154A, arm 154B, arm 154C, and arm 154D. These arms are arranged in such a way that the spaces between them create one or more slots. In the figure, the space created by arms 154A and 154B on one side, and arms 154C and 154D on the other side is first slot 156. In some embodiments, a wire (e.g., an archwire) can be placed (e.g., inserted, threaded, positioned) into this first slot. Second slot 158 is formed by the arms 154B and 154C on one side and the arms 154A and 154D on the other side. In some embodiments, this second slot can also be used to place a wire. Also shown as part of bracket 170 in this figure are the extensions. Extension 164B is seen as a wing of arm 154B, extension 164C as a wing of arm 154C, and extension 164D as a wing of arm 154D. Extension 164A is the wing of arm 154A. These extensions are overhangs that can allow placement of a ligating member (such as a ligating module, which can be a donut shaped plastic piece that ties in an archwire to the bracket). Other than the bracket, in FIG. 9, the frame is shown. Frame 180A is seen to have receiving member 114A, anchoring member 112A, and clip 124A. Anchoring member is the part of the frame that is closest to the tooth surface, and the receiving member is the part that is closer to the bracket arms. The clip materially is not a separate piece in this embodiment, and is seen to be an extension of the anchoring member. Because the clip constitutes the fastener, and because the fastener is integral to the frame, in this embodiment, frame 180A and frame member 110A are not practically distinct. In other embodiments, it will become clear that when fastener includes additional items (such as screws), the frame member is mostly comprised by anchoring and receiving members, whereas the frame is comprised by not only the anchoring and receiving members, but also by the fastener (e.g., a screw).

The fastener shown in FIG. 9 is seen to have clip teeth 124B that lock against receiving teeth 124C of the receiving member. Clip 124A is also seen to have stopper 124D and clip opening 124E. The stopper ensures that even if the clip teeth lose their grip, the receiving member will not be substantially removed from the anchoring member. The clip opening is an optional feature, and in some embodiments can be eliminated.

Also seen in FIG. 9 are hinge 116A and groove 130A. The hinge connects the receiving and the anchoring members and allows relative movements of the two in order to accommodate insertion and removal of a bracket. The hinge can be manufactured from the same materials as the rest of the frame, and need not be a separate piece. In certain embodiments, the hinge can be a separate piece. Groove 130A is the compartment between the receiving and the anchoring members within which the base of the bracket is accommodated. Even though shown as open through the entire length of the area of the receiving member, the groove can be blocked from the sides in some embodiments. For example, either the receiving member or the anchoring member, or both can have an extension on the side that when the two members are closed onto each other, essentially closes one or more sides of the groove.

The term "closed" or "closing" in the context of the two members, the receiving and the anchoring members, is used to refer to the relative state of the two members when the receiving member cannot easily receive a bracket. As should be apparent, the two members need to be, at least slightly, pried open so that a bracket can be inserted without significant friction. Such a state, in which a bracket can be inserted and removed without significant friction, is referred to as the "open" state of the frame. On the other hand, the terms "lock", "locked", etc. are used to relate to the state of the receiving members and anchoring members when they are secured to prevent accidental or unwanted movement of the bracket. The terms "unlock", "unlocked", etc. relate to the state of the mentioned members when the bracket can be moved relative to the frame as desired. When the frame is locked with a bracket inside, a patient cannot simply pull and remove a bracket from the frame while leaving all the parts intact.

Figure 10:
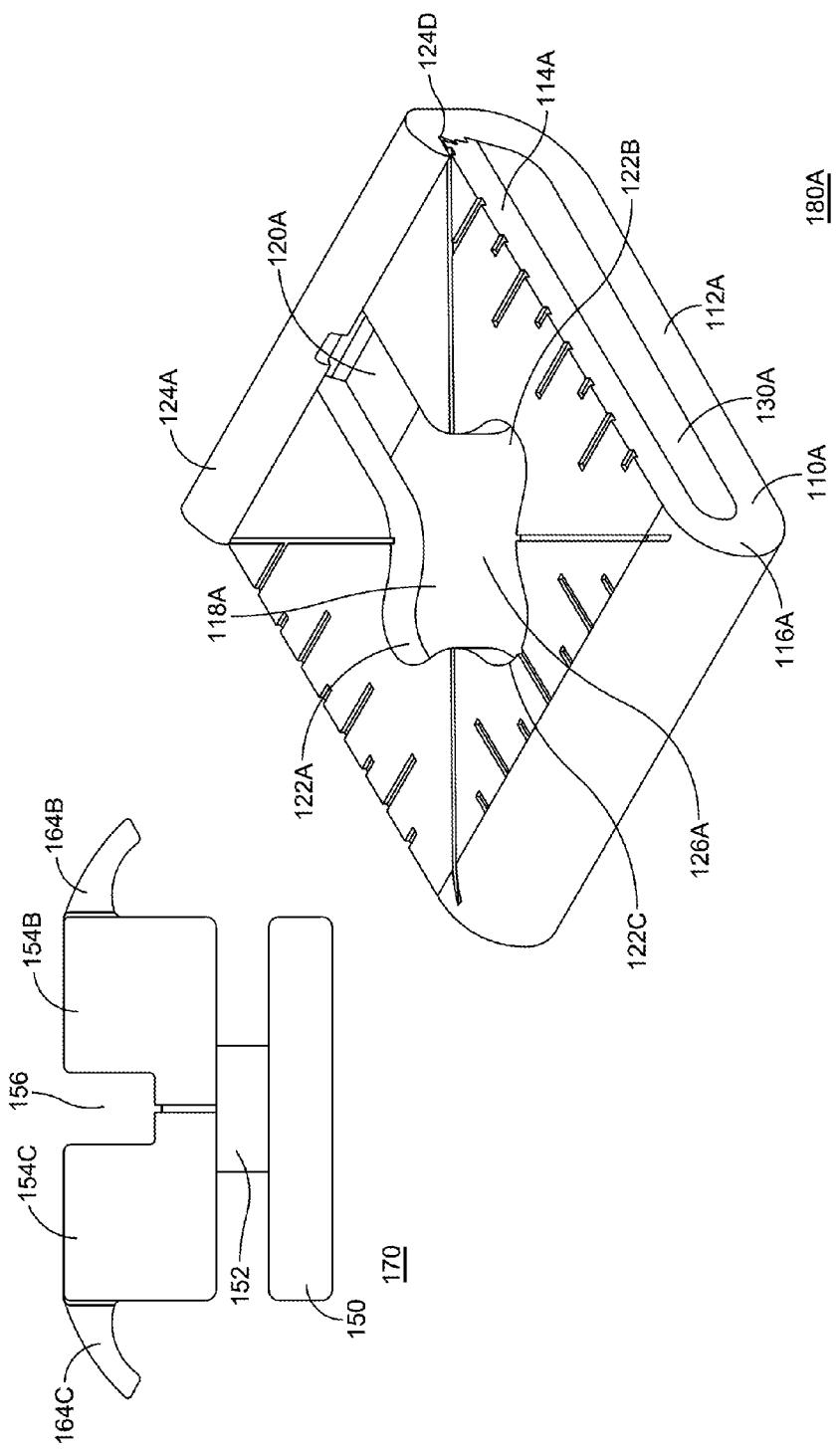
FIG. 10 is a schematic of perspective views of an embodiment of the bracket system showing a bracket and a frame as separated components.

Now referring to FIG. 10, the left side shows bracket 170 and the right side shows frame 180A. As shown in this side view, bracket 170 has base 150 and neck 152, in addition to having the arms and extensions mentioned during the discussion of FIG. 9. First slot 156 is clearly visible between arm 154B and arm 154C. A wire can be placed into that slot and then stabilized via a variety of methods (e.g., ligating modules that make use of the extensions, or additional covers that go above the slot). Neck 152, referred to as a stem in some other embodiments, connects the base of the bracket with the arms of the bracket. The neck can be substantially surrounded by the receiving member once the bracket is in place within a frame. Base 150, once a bracket is placed into the groove (also called compartment in other embodiments) of a frame, rests against the inner surface of the anchoring member. In some embodiments, either one or both of the inner surface of the anchoring member and the bottom surface of the base are manufactured as a textured surface in order to increase the friction when they come together. This aids in stabilizing the relative positions of the two.

On the right side of FIG. 10, frame 180A is shown with opening 118A, neck opening 120A, interior surface 126A, lobe 122A, lobe 122B, and lobe 122C. Opening 118A is where the bracket will be rested once in place. Within the opening, the bracket has freedom to move, provided that the frame is in an unlocked position. The neck opening is designed to allow insertion of the bracket into the frame. Upon prying apart at either the clip or the receiving member, depending on the embodiment used, a bracket can be slid through neck opening 120A and positioned within opening 118A. Interior surface 126A can be textured to increase the frictional grip it has on the bracket. The lobes can be arranged in any way, and there can be fewer or more than three lobes. In an embodiment, the lobes confer an enhanced degree of movement to the bracket. For example, in the figure shown, the bracket can be positioned along any of the four directions: toward lobe 122A, toward lobe 122B, toward lobe 122C, or toward neck opening 120A. Also, the bracket can be rotated clockwise or counterclockwise within the opening. The ability to move in these various directions is useful because by placing a bracket in a different location with respect to the tooth, a different force can be exerted onto the tooth, effectively moving it in a different way.

Figure 11:
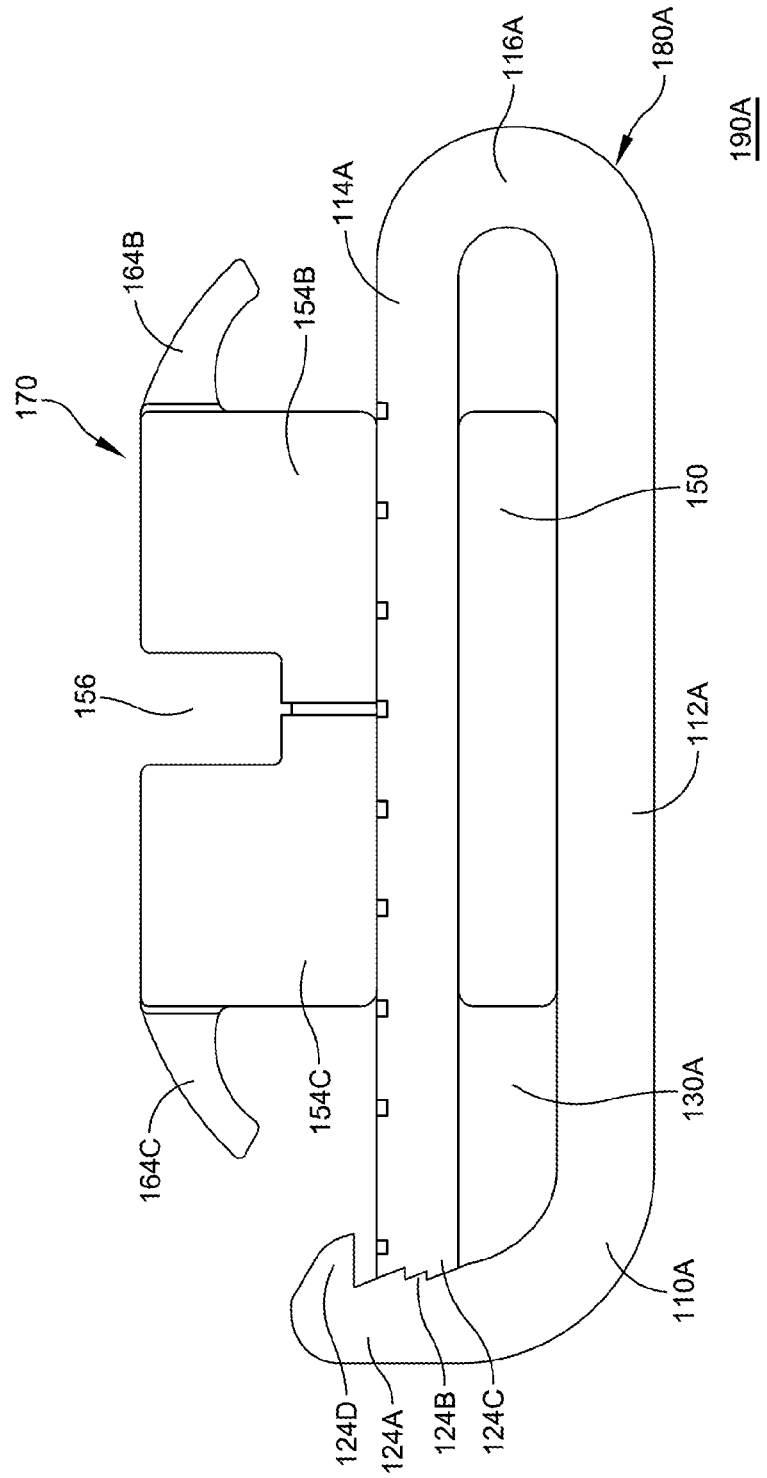
FIG. 11 is a schematic of a side view of an embodiment of the bracket system.

Turning our attention to FIG. 11, bracket system 190A is shown from a side view. This view clearly shows the interlocking clip teeth 124B and receiving teeth 124C. Stopper 124D is also shown to stop any potential movement beyond a certain level, in case the clip teeth or the receiving teeth suffer a trauma and are unable to lock the frame. Base 150 of the bracket is seen to be placed into groove 130A of the frame. In this figure, the first slot, which can accept a wire, is seen to be in a direction parallel to that of the clip. This is not mandatory, as will become clear with inspection of the next figure.

Figure 12:
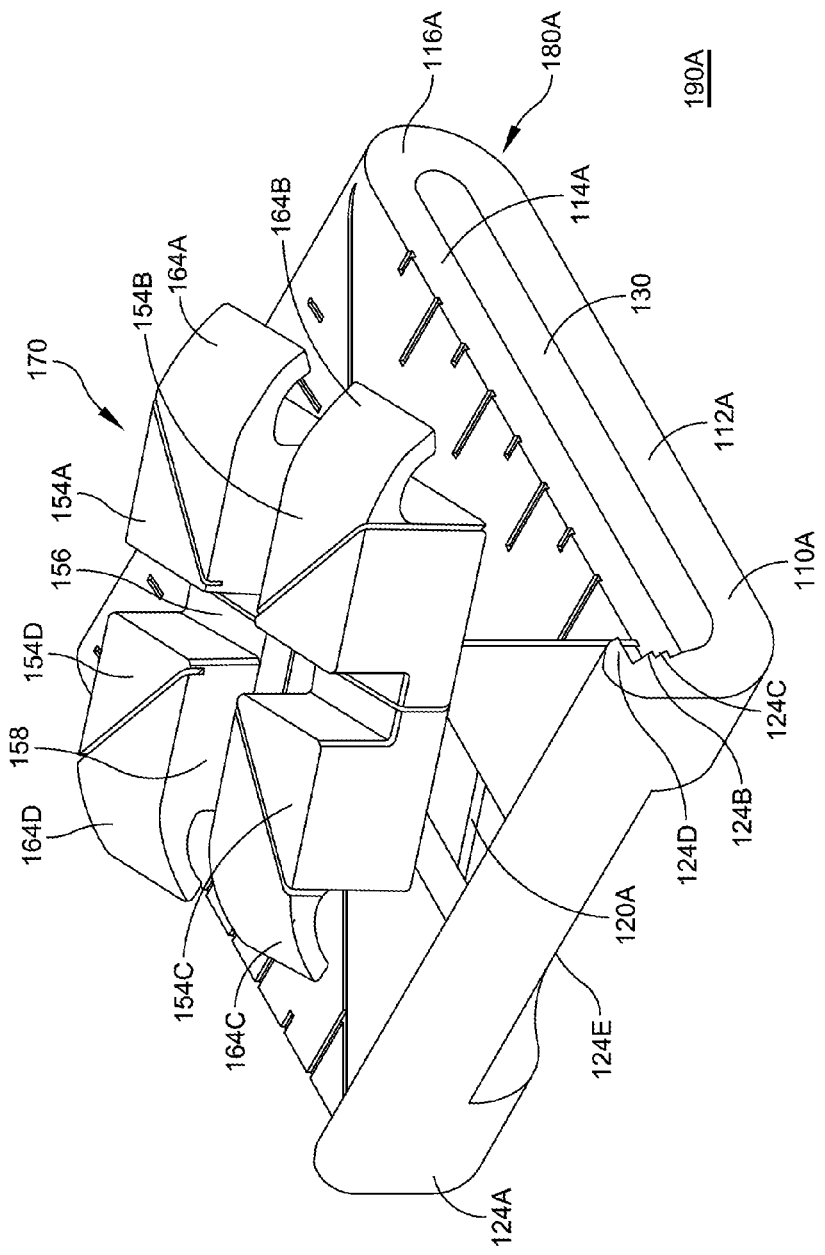
FIG. 12 is a schematic of a perspective view of an embodiment of the bracket system showing a bracket that is rotated differently relative the one shown in FIG. 9.

FIG. 12 shows bracket system 190A from a perspective view, this time with bracket 170 rotated to a different degree than the one shown in FIG. 9. From this drawing, it should be apparent that the bracket can be rotated to any degree (e.g., 0 to 360 degrees). In any of these rotated orientations, any of the slots (first slot 156 or second slot 158) can be used to accommodate an archwire. In addition to rotating the bracket around a range of 360 degrees, the bracket can also be moved (translated) toward any of the 360 degrees. Even though the highest level of movement will be allowed in the directions corresponding to those of the lobes, some movement toward other directions can also be permitted in certain embodiments. A range of rotations and movements is possible with bracket being able to move within the lobes and rotate the within frame.

Figure 13:
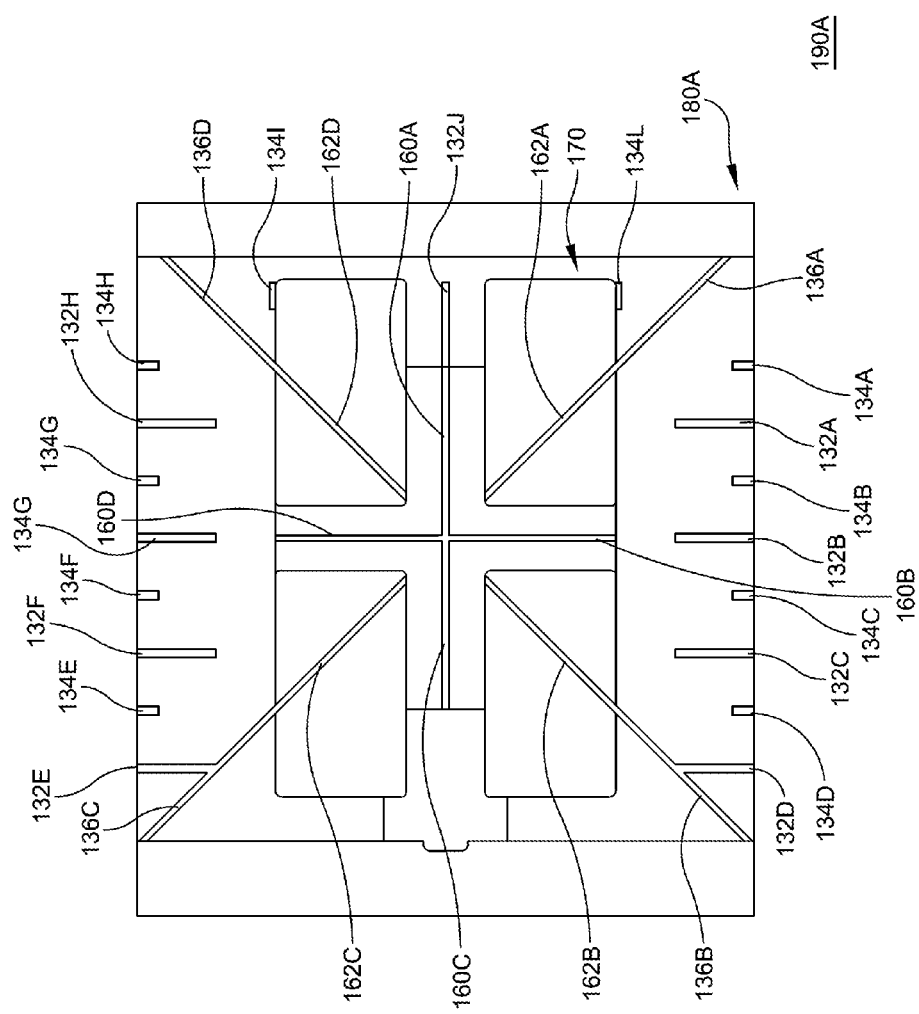
FIG. 13 is a schematic of a top view of an embodiment of the bracket system showing the relative alignments of different markings on a bracket with those on a frame.

FIG. 13 shows a top view of bracket system 190A, which shows one embodiment having markings on the bracket and the frame to assist the dental practitioner in aligning the bracket. In this figure, the relative alignment is achieved with the coarse orthogonal markings, fine orthogonal markings, and oblique markings of the frame with the orthogonal bracket markings and oblique bracket markings. Coarse orthogonal markings 132A through 132K are in a perpendicular direction to an edge of the receiving member (marks 132I and 132K are not visible in the figure). Fine orthogonal markings 134A through 134L are also in a perpendicular direction to an edge of the receiving member, but are shorter than the coarse orthogonal markings (marks 134J and 1343K are not visible in the figure). Such an arrangement can be used, for example by first aligning the bracket against the coarse markings and then against the fine ones to increase the precision. In addition to these orthogonal markings, the receiving member is also shown to have oblique markings 136A through 136D. Any of these markings can be of use during both the rotational and translational movements of the bracket with respect to the receiving member. To make it easier to register the bracket against these markings, the bracket itself can have markings. The figure shows bracket 170 to have orthogonal bracket markings 160A through 160D and oblique bracket markings 162A through 162D. A clinician can record and keep track of the relative alignments of these against each other throughout the duration of a treatment. That way, an accurate history of the progress of the forces applied on a tooth will be available, which can be used to further increase the precision of the orthodontic treatment.

Figure 14:
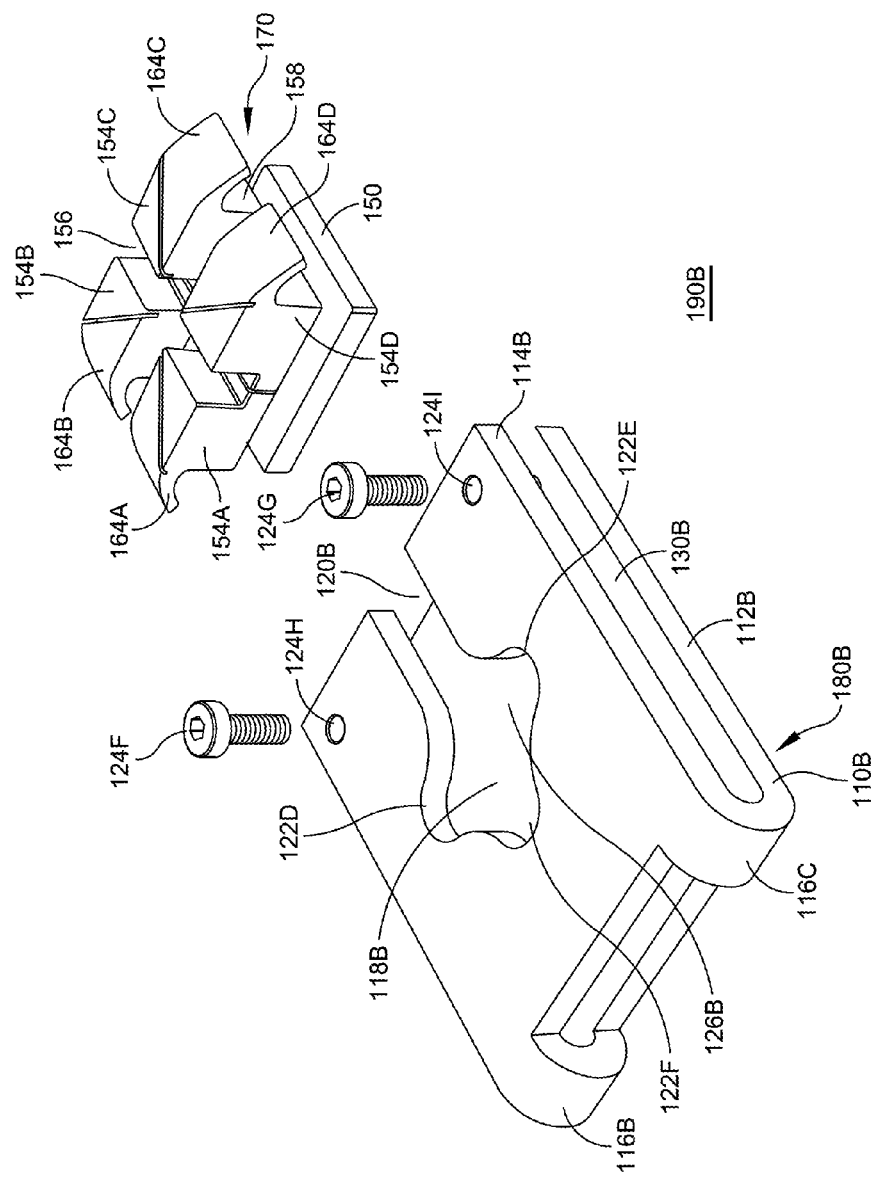
FIG. 14 is a schematic of a perspective view of an embodiment of the bracket system that is different than the one shown in FIG. 9 through FIG. 13. This particular bracket system is shown with its bracket and frame as separated components. The figure also shows two screws that are used to fasten the frame once it receives the bracket.

Referring now to FIG. 14, an additional embodiment of the bracket system is displayed in a perspective view, with its components shown separately. Bracket system 190B is shown with bracket 170, frame 180B, first screw 124F, and second screw 124G. In this embodiment, instead of the clip that was used in the embodiments shown in figures FIG. 9 through FIG. 13, screws and screw receivers are used. A screw receiver is a hole having a complementary thread to the helical ridge of a screw. Screws, depending on their design, can be tightened by clockwise or counterclockwise rotation, and then untightened by an opposite rotation. The combination of screw 124F, screw 124G, and frame member 110B constitutes frame 180B. Screw 124F is initially received by first screw receiver 124H, which can have a complementary interior surface to snugly receive first screw 124F. Similarly, second screw 124G is initially received by second screw receiver 124I. To achieve the locking of the frame, each screw is ultimately received by an additional screw receiver. First screw 124F is received by third screw receiver 124J, and second screw 124G is received by fourth screw receiver 124K (shown in FIG. 16). The third and fourth screw receivers do not need to extend along the full width of the anchoring member, although they can if the screws are manufactured with a limited length so that they will not protrude from the anchoring side toward the tooth. In some embodiments, only the third and fourth screw receivers have spirally accommodating grooves for the screws, and the first and second receivers are merely holes through which the screws can pass.

FIG. 14 also shows parts that are analogous to those shown in prior embodiments. Examples of parts shown are lobes 122D through 122F, groove 130B, anchoring member 112B, receiving member 114B, frame member 110B, opening 118B, neck opening 120B, and bracket 170 with similar parts. Unlike the previous embodiment shown, this one has two hinges: hinge 116B and hinge 116C. In some embodiments, there can be fewer or more hinges. Similarly, in alternative embodiments, there can be fewer or more screws and screw receivers. Screws can be placed anywhere along the frame, as long as they stabilize, or do not prevent stabilization of a bracket. This figure intuitively illustrates how a bracket can be inserted onto a frame though the neck opening of the frame and the how the frame can be locked to stabilize the bracket.

Figure 15:
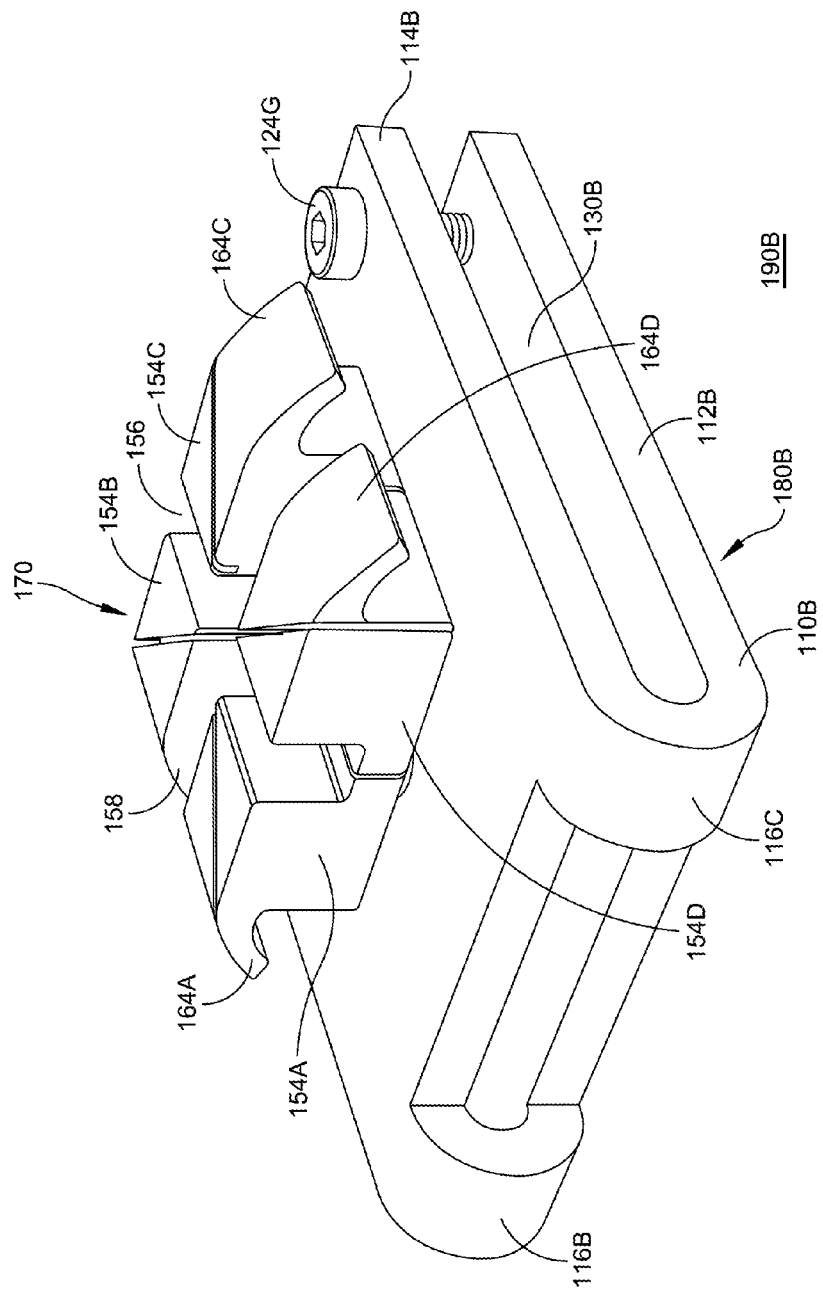
FIG. 15 is a schematic of a perspective view of an embodiment of the bracket system that shows the components of the system together. These components were shown in their separated states in FIG. 14.

Directing our attention to FIG. 15, bracket system 190B is shown with the bracket 170 and frame 180B, as they fit together. Screw 124G is seen to extend along groove 130B all the way to the fourth screw receiver. First slot 156 formed between arms 154A with 154B on one side and 154C with 154D on the other side is shown to be perpendicular to the direction from one screw to the other. Similar to other embodiments, another slot can be used, as well as the first slot, to place a wire. Again similarly, the bracket can be rotated or translated, or rotated and translated in any direction that is within a plane parallel to the plane of the receiving member.

Figure 16:
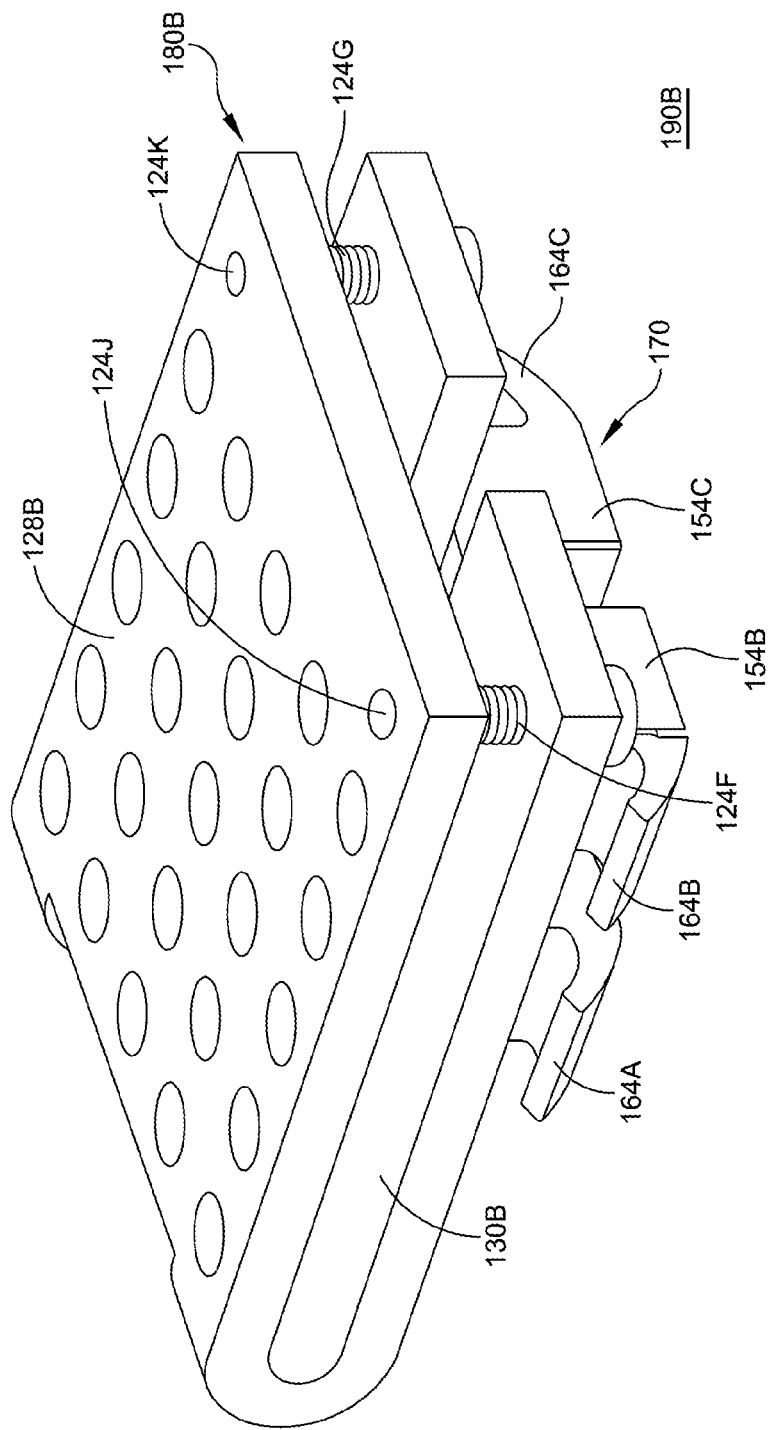
FIG. 16 is a schematic of a perspective view of an embodiment of the bracket system. The figure shows the embodiment shown in FIG. 15 from its opposite side, essentially revealing the exterior surface of its frame that can contact a tooth.

Referring to FIG. 16, bracket system 190B is shown in a perspective view that makes apparent the exterior surface of the frame that contacts a tooth. This view is upside-down compared to the one in FIG. 15. Exterior surface 128B is shown to have a series of circular depressions. A variety of texture features can be used on the exterior surface on any of the embodiments described herein. In addition to depressions, projections, recesses, general roughness, and any regular or irregular features, pure or together with other kinds of features can be used, as long as the final exterior surface has a better frictional interaction, to any degree, with a tooth surface than an exterior surface with no features. In an embodiment of using the bracket system, a clinician leaves the frame on the tooth for the entire duration of the treatment, which can last up to years, and only adjusts the bracket during certain intervals. Because the frame only will need to be removed once, at the end of the treatment, the bonding between a tooth and the exterior surface can be strong.

Figure 17:
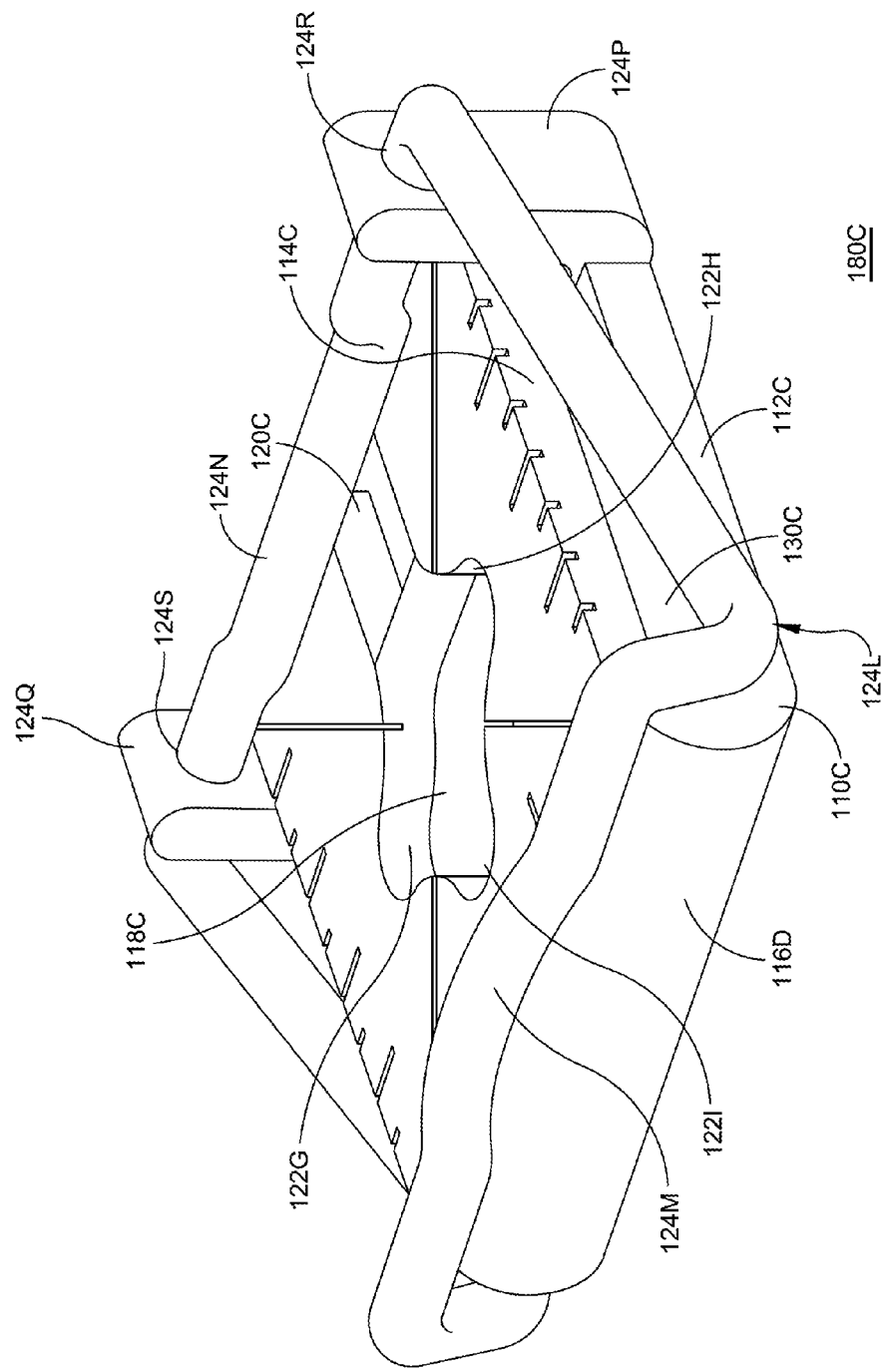
FIG. 17 is a schematic of a perspective view of an embodiment of the bracket system that is different than the one shown in FIG. 9 through FIG. 13, and also different from the one shown in FIG. 14 through FIG. 16. This particular embodiment uses a lever, as shown, to fasten the frame. The figure only shows the frame component; the bracket component has been removed to better illustrate different parts of the lever.

Now looking at FIG. 17, the frame part of a yet another embodiment of the bracket system is shown. In parallel with the previously discussed embodiments, the frame is stabilized by a fastener; however, in contrast to the previous embodiments, the fastener is a lever and not a screw or a clip, in the sense of the previous embodiments. Frame 180C is shown having lever 124L. Lever 124L is attached to the frame at first lever support 124P and at second lever support 124Q. The lever, shown overall to have a shape of an irregular tube herein, is threaded in this embodiment through first lever receiver 124R and second lever receiver 124S. First lever receiver 124R is a hole within first lever support 124P, and second lever receiver 124S is a hole within second lever support 124Q. Lever 124L can rotate through the two lever receivers such that it can reach near the hinge from the receiving member side as shown. The depicted embodiment is a locked position of the frame. Locking action is accomplished by lever lock 124N, which is the part of the lever that applies pressure on the side of the receiving member that is near neck opening 120C. As seen, lever lock is a segment of the lever that longitudinally protrudes away from the lever in such a way that when the lever is closed toward hinge 116D, the lever lock presses onto the receiving member. Also shown in this figure are lobes 122G though 122I, groove 130C, frame member 110C, anchoring member 112C, receiving member 114C, and opening 118C. The part of the handle that can be moved, manually or with a tool, is designated as lever handle 124M. Lever handle can be the entire accessible length of the lever other than the lever lock, or it can be just the part of the lever that extends along the hinge when closed, depending on the embodiment.

Figure 18:
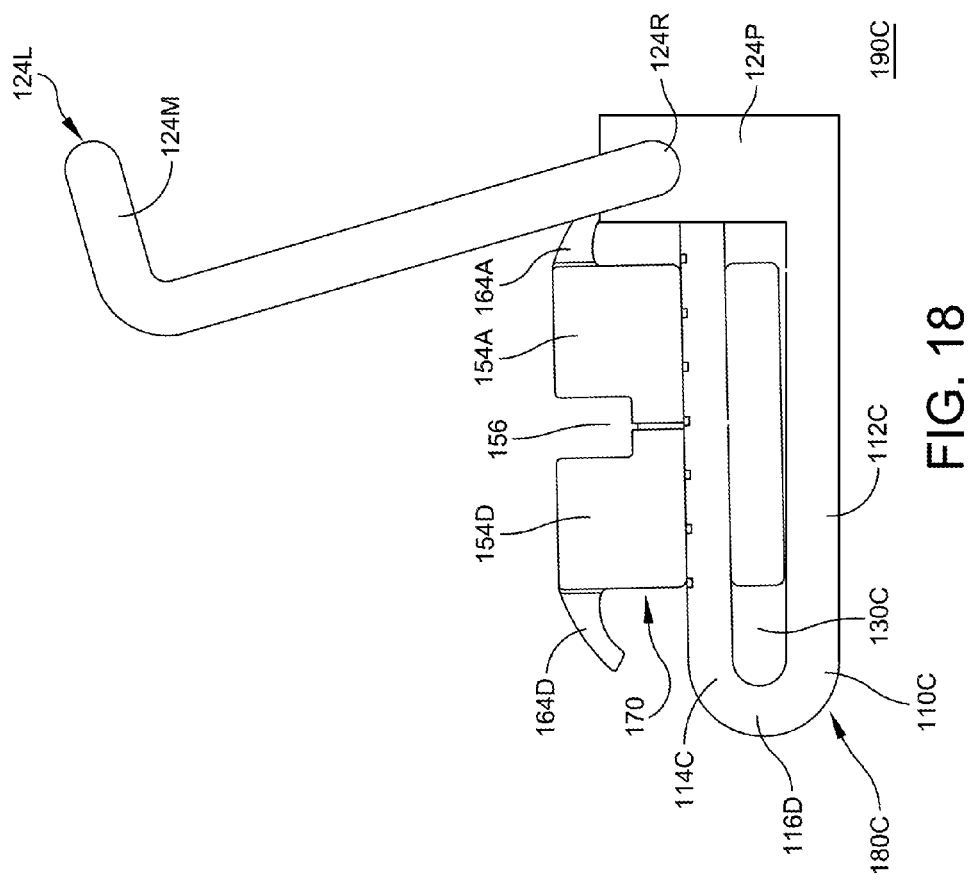
FIG. 18 is a schematic of a side view of an embodiment of the bracket system, part of which is also shown in FIG. 17.

FIG. 18 shows bracket system 190C with lever 124L in a position that displays frame 180C in an unlocked position. As seen, in contrast to FIG. 17, when the lever is lifted away from hinge 116D, receiving member 112C is free to move away from anchoring member 114C, effectively freeing bracket 170 to move or rotate within the opening. A clinician can lift lever handle 124M, adjust bracket 170, and then lock the lever handle by closing it toward hinge 116D. Even though the figure shows first slot 156 to be positioned in the direction along the hinge, as should be apparent from the ability of the bracket to translate or rotate in any direction, the first slot can be aligned in any direction. In some embodiments, the second slot can be used as well, either to thread a wire through or to stabilize a wire threaded through the first slot. Locking can be effected by motions of the lever to positions other than the one shown in the figures as well.

The described embodiments can be used to move a tooth in a variety of directions, as described. Additional components can be added to the bracket system. For example, metallic ligatures, elastic ligatures, or a self-ligating system component can be used to ensure stabilization of a wire. Other related components that can be used are bands, molar tubes, elastomeric products, coil springs, lingual arches, extra-oral appliances, and retainers. In some embodiments, the bracket component of the bracket system can have a base that is so slanted to result in the slot being angled in different ways relative to the surface of the tooth, and positioned in different ways relative to the center of resistance of the tooth. Alternatively, the arms and the surface of the neck that is away from the base can be manufactured in ways that would result in a desired slanting. The neck and the arms can also be manufactured in ways that can increase or decrease the distance between the base of the bracket and the area accessible to a wire within the slot. That would effectively result in movements of the bracket toward or away from a surface of a tooth. It is also possible to use an external item to be placed between the bracket and the frame, so as to obtain alternative arrangements of the bracket system. In some embodiments, the bracket can have a single slot, whereas, in others, in can have more than two slots. The bracket, in certain embodiments, can have fewer than four or more than four arms.

In alternative embodiments, the bracket system can include at least two components: a frame and a slot component. On one side (e.g., the exterior side), the frame can be bonded to the tooth surface with the use of an adhesive material commonly used in orthodontics. The frame can have a shape that bends on itself and creates a compartment (e.g., groove) in which the slot component (e.g., bracket) can move. The bracket slot component can include a stem (e.g., neck), a base, and a top portion where the slot and other components of a normal bracket lie. The stem can be positioned immediately below the top portion of the bracket and can be accommodated in the opening of the frame. The base of the bracket component can be below the stem and can fit into the groove of the frame as it lies atop a textured interior (e.g., interior surface) of the bracket frame. The textured interior can ensure that the bracket component does not move freely within the space (e.g., groove, compartment) created by the bracket frame. The diameter of the bracket stem can be smaller than the opening created by the frame such that the bracket stem fits within the opening. The base of the stem can be wider than the stem, and can be narrower than the frame. When the frame is in passive form, or when the bracket system is unlocked, vertical pressure is relieved from the slot component, and less frictional force (or no substantial frictional force) is generated between the base of the component and the textured interior surface of the frame. When the frame is in active form, or when the bracket system is locked, the distance between the two members of the frame (one designed to be adhered to a tooth, and the other designed to receive the bracket) is decreased such that the bracket base is constrained between the two members so that it cannot freely move. This can create an increased vertical pressure and can increase the frictional force between the slot component base and the frame's textured interior surface to the point that the slot becomes substantially stationary.

According to this particular embodiment explained above, when the frame is unlocked, the slot component can freely rotate 360 degrees around the central longitudinal axis (e.g., the axis that extends along the direction between the center of the base and the center of the bracket slot) of the stem. The slot can also slide (as the arms slide) to any direction within the area defined by the frame boundaries, and to the limit that the slot stem comes in contact with the frame boundaries.

The exterior surface of the frame that is designed to contact a tooth (e.g., the exterior surface of the anchoring member) can be serrated, meshed, or made rough in any other way to increase bond strength. The exterior surface of the frame that is designed to contact a tooth can have adaptive curves associated with the morphology of tooth surface, whereas the side of the frame that faces the bracket (e.g., the exterior surface of the frame that is closest to the slot of the bracket) need not be so morphologically processed. The bottom surface of the bracket base and the base-facing-side of the frame (e.g., the interior surface) can have micro-projections, or other friction enhancing properties, to prevent or reduce the probability of sliding of the slot when the frame is locked. In some embodiments, there also is a high frictional coefficient between the bottom part of the arms and the top external part of the receiving members.

Locking the frame can be accomplished by a variety of mechanisms. For example, screws can be used. Tightening of the screws can create vertical pressure between the frame components that hold the slot component and this can lead to increased friction between the bracket base and frame's textured interior surface to the point at which the slot component becomes substantially stationary (e.g., does not move more than 1%, 2%, 3%, 4%, 5%, 10% of its length in any direction in a given day, week, or month).

Another method of locking the frame can incorporate an undercut (e.g., a clip that extends from the part of the frame that is set to contact a tooth) as a part of the frame. Similar to the way a locking pin (e.g., a screw, as described) can work, the component of the frame that is designed to be away from a tooth can be squeezed under the undercut, which can create a desired vertical pressure necessary to increase a frictional force to prevent the slot component from substantially moving.

Another feature found in some embodiments of the present invention is the presence of markings on the bracket as well as the frame. Markings can be placed anywhere on any of the components of the bracket system. These markings can allow a user to quantify the amount of movement in any direction. Borders of the frame can be marked similar to those of a ruler and the bracket can have reference points. At any given time, a user can determine the amount of movement in any direction by comparing the position of the reference points (e.g., orthogonal bracket markings, oblique bracket markings) on the bracket with the measurements (e.g., coarse orthogonal markings, fine orthogonal markings, and oblique markings) on the frame. This can also allow a user to reset the bracket tip and torque at any given time by aligning the bracket with the frame.

The present invention involves methods of using bracket system described herein. The steps of the method include anchoring the frame of the bracket system onto the tooth using an adhesive (e.g., bonding material). An embodiment of the method of the present invention includes placing the bracket into the frame and fastening the frame to lock the bracket into a position. The way the bracket is locked into position varies depending on the frame being used, but, for example, the frame can be fastened using the clip, screws or lever, as described herein. The steps of the method include positioning the bracket in the frame (e.g., within one of the lobes and/or rotating the bracket) to achieve the desired movement and positioning of the teeth. Once the bracket is in place, the teeth are allowed to move for a period of time (e.g., about 1 day to about 3 months, and preferably between about 1 and about 4 weeks) until the next adjustment of the bracket. At the next visit, the dental practitioner does not need to re-position the frame and rebond the frame to the tooth. The dental practitioner simply readjusts the bracket within the frame by unlocking the frame, re-positioning the bracket, and locking the frame. Accordingly, the method of the present invention further includes re-positioning the bracket without having to rebond the frame, which can be done repeatedly over a multitude of visits, to allow the teeth to continue to move into the desired position.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A bracket system for use as part of orthodontic braces, the bracket system comprising:
   a) a bracket that comprises:
      i) one or more arms that form one or more slots that can receive a wire;
      ii) a neck; and
      iii) a base; and
   b) a frame configured to receive the bracket, wherein the frame comprises:
      i) an anchoring member that can anchor the frame to a tooth;
      ii) a receiving member that has a plane that extends along the receiving member, wherein the receiving member is adapted to receive the bracket;
      iii) an opening along the plane of the receiving member through which the bracket can be received, wherein the opening is shaped to allow linear movement of the bracket along the plane as well as rotation of the bracket about an axis that is perpendicular to the plane; and iv) a fastener that, when engaged, places the bracket system into a locked position, and when disengaged places the bracket system into an unlocked position; wherein the bracket is adapted to be received by the frame, and wherein once the frame is attached to the tooth on a patient and the bracket system is in an unlocked position, the bracket can be rotated about the axis that is perpendicular to the plane, and can be moved into more than one position by moving the bracket linearly along the plane of the receiving member without the frame being removed from or reattached to the tooth.

2. The bracket system of claim 1, wherein the exterior surface of the frame that comes into contact with a tooth is textured such that it has a high frictional coefficient when contacting the tooth.

3. The bracket system of claim 2, wherein the interior surface of the frame that comes into contact with the bottom surface of the base, or the bottom surface of the base that comes into contact with the interior surface of the frame, or both said interior surface of the frame and said bottom surface of the base are textured in such a way that they have a high frictional coefficient when contacting one another.

4. The bracket system of claim 1, wherein the bracket has four arms.

5. The bracket system of claim 1, wherein the bracket can be unlocked from the frame in any orientation, can be rotated to any orientation, and can be locked into any orientation, wherein the orientations comprise translations and rotations of the bracket with respect to the frame, wherein the rotations are between the degrees of zero and three-hundred-and-sixty in the plane of the receiving member, and wherein the translations are in the direction of any said degrees.

6. The bracket system of claim 5, wherein the fastener is a clip, and wherein the entire frame, including the clip, receiving member, and the anchoring member are made substantially as a single-piece.

7. The bracket system of claim 6, wherein the clip has clip-teeth that lock in with receiving-teeth on the receiving member.

8. The bracket system of claim 5, wherein the clip further comprises a stopper to further stabilize a closed position of the anchoring member and the receiving member.

9. The bracket system of claim 1, further comprising frame-markings on the frame and bracket-markings on the bracket, wherein the frame-markings and the bracket-markings, when aligned relative to each other, enable accurate positioning of the bracket within the frame.

10. The bracket system of claim 1, wherein one or more components of the bracket system are substantially made, in part or in whole, from nickel-titanium alloys, titanium-molybdenum alloys, stainless steel, or a combination thereof.

11. A bracket system for use as part of orthodontic braces, the bracket system comprising:
a) a bracket that comprises:
  i) one or more arms that form one or more slots that can receive a wire;
  ii) a neck; and
  iii) a base; and
b) a frame configured to receive the bracket, wherein the frame comprises:
  i) an anchoring member that can anchor the frame to a tooth;
  ii) a receiving member that has a plane that extends along the receiving member, wherein the receiving member is adapted to receive the bracket;
  iii) an opening along the plane of the receiving member through which the bracket can be received, wherein the opening is shaped to allow linear movement of the bracket along the plane as well as rotation of the bracket about an axis that is perpendicular to the plane, wherein the opening has three lobes and a side that opens to an edge of the receiving member; and
  iv) a fastener that, when engaged, places the bracket system into a locked position, and when disengaged places the bracket system into an unlocked position; wherein the bracket is adapted to be received by the frame, and wherein once the frame is attached to the tooth on a patient and the bracket system is in an unlocked position, the bracket can be rotated about the axis that is perpendicular to the plane, and can be moved into more than one position by moving the bracket linearly along the plane of the receiving member without the frame being removed from or reattached to the tooth.

12. The bracket system of claim 11, wherein the frame can be attached to the lingual side or the facial side of a tooth.

13. The bracket system of claim 11, wherein the bracket has a self-locking feature.

14. The bracket system of claim 11, wherein when the bracket system is in a locked position, the bracket, relative to the frame, cannot move more than 1% of the average length of the bracket.

15. The bracket system of claim 11, wherein the fastener places the bracket system into a locked position by fixing the receiving member to the anchoring member.

16. A method of using a bracket system, comprising:
a) anchoring a frame of the bracket system onto the tooth, wherein the bracket system comprises:
  i) a bracket that comprises:
    (1) one or more arms that form one or more slots that can receive a wire;
    (2) a neck; and
    (3) a base; and
  ii) the frame configured to receive the bracket, wherein the frame comprises:
    (1) an anchoring member that can anchor the frame to a tooth;
    (2) a receiving member that has a plane that extends along the receiving member, wherein the receiving member is adapted to receive the bracket;
    (3) an opening along the plane of the receiving member through which the bracket can be received, wherein the opening is shaped to allow linear movement of the bracket along the plane as well as rotation of the bracket about an axis that is perpendicular to the plane; and
    (4) a fastener that, when engaged, places the bracket system into a locked position, and when disengaged places the bracket system into an unlocked position, wherein the bracket is adapted to be received by the frame, and wherein once the frame is attached to the tooth on a patient and the bracket system is in an unlocked position, the bracket can be rotated about the axis that is perpendicular to the plane, and can be moved into more than one position by moving the bracket linearly along the plane of the receiving member without the frame being removed from or reattached to the tooth;
b) placing the bracket into the frame; and
c) fastening the frame to lock the bracket into a position.

17. The method of claim 16, wherein the method further comprises unfastening the frame, moving the bracket, and then fastening the frame to lock the bracket into a new position.

18. The method of claim 16, wherein the method further comprises unfastening the frame, rotating the bracket in the plane of the receiving member, and then fastening the frame to lock the bracket into a new position.

19. The method of claim 16, wherein the method further comprises unfastening the frame, rotating the bracket in the plane of the receiving member, moving the bracket, and then fastening the frame to lock the bracket into a new position.

20. A method of using a bracket system, comprising:
   a) placing a bracket into a frame that is anchored to a tooth, wherein the bracket system comprises:
      i) the bracket that comprises:
         (1) one or more arms that form one or more slots that can receive a wire;
         (2) a neck; and
         (3) a base; and
      ii) the frame configured to receive the bracket, wherein the frame comprises:
         (1) an anchoring member that can anchor the frame to a tooth;
         (2) a receiving member that has a plane that extends along the receiving member, wherein the receiving member is adapted to receive the bracket;
         (3) an opening along the plane of the receiving member through which the bracket can be received, wherein the opening is shaped to allow linear movement of the bracket along the plane as well as rotation of the bracket about an axis that is perpendicular to the plane, wherein the opening has three lobes and a side that opens to an edge of the receiving member; and
         (4) a fastener that, when engaged, places the bracket system into a locked position, and when disengaged places the bracket system into an unlocked position, wherein the bracket is adapted to be received by the frame, and wherein once the frame is attached to the tooth on a patient and the bracket system is in an unlocked position, the bracket can be rotated about the axis that is perpendicular to the plane at degrees from 0 to 360, and can be moved into more than one position by moving the bracket linearly along the plane of the receiving member without the frame being removed from or reattached to the tooth; and
   b) fastening the frame to lock the bracket into a position.

21. A kit for using as a part of orthodontic braces, the kit comprising:
   a) a frame, wherein the frame comprises:
      i) an anchoring member that can anchor the frame to a tooth;
      ii) a receiving member that has a plane that extends along the receiving member, wherein the receiving member is adapted to receive the bracket;
      iii) a hinge that connects the anchoring member and the receiving member in an adjustable way;
      iv) an opening along the plane of the receiving member through which the bracket can be received, wherein the opening is shaped to allow linear movement of the bracket alone the plane as well as rotation of the bracket about an axis that is perpendicular to the plane; and
      v) a fastener that, when engaged, places the bracket system into a locked position, and when disengaged places the bracket system into an unlocked position; and
   b) a bracket, wherein the bracket comprises:
      i) one or more arms;
      ii) a neck; and
      iii) a base, wherein the base, in part or in whole, can be received by the frame, wherein the one or more arms form one or more slots that can receive a wire, wherein the bracket is adapted to be received by the frame, and wherein once the frame is attached to the tooth on a patient and the bracket system is in an unlocked position, the bracket can be rotated about the axis that is perpendicular to the plane, and can be moved into more than one position by moving the bracket linearly along the plane of the receiving member without the frame being removed from or reattached to the tooth.

22. A bracket system for use as part of orthodontic braces, the bracket system comprising:
   a) a bracket that comprises:
      i) one or more arms that form one or more slots that can receive a wire;
      ii) a neck; and
      iii) a base; and
   b) a frame configured to receive the bracket, wherein the frame comprises:
      i) an anchoring member that can anchor the frame to a tooth;
      ii) a receiving member that has a plane that extends along the receiving member, wherein the receiving member is adapted to receive the bracket;
      iii) an opening along the plane of the receiving member through which the bracket can be received, wherein the opening is shaped to allow linear movement of the bracket along the plane as well as rotation of the bracket about an axis that is perpendicular to the plane; and
      iv) a fastener that, when engaged, places the bracket system into a locked position, and when disengaged places the bracket system into an unlocked position, wherein the fastener comprises one or more screws and one or more screw receivers;
   wherein the bracket is adapted to be received by the frame, and wherein once the frame is attached to the tooth on a patient and the bracket system is in an unlocked position, the bracket can be rotated about the axis that is perpendicular to the plane, and can be moved into more than one position by moving the bracket linearly along the plane of the receiving member without the frame being removed or reattached to the tooth.

23. The bracket system of claim 22, wherein the fastener comprises two screws and four screw receivers, wherein each screw can pass through one screw receiver in the receiving member and at least partially pass into one screw receiver in the anchoring member.

24. A bracket system for use as part of orthodontic braces, the bracket system comprising:
   a) a bracket that comprises:
      i) one or more arms that form one or more slots that can receive a wire;
      ii) a neck; and
      iii) a base; and
   b) a frame configured to receive the bracket, wherein the frame comprises:

i) an anchoring member that can anchor the frame to a tooth;
ii) a receiving member that has a plane that extends along the receiving member, wherein the receiving member is adapted to receive the bracket;
iii) an opening along the plane of the receiving member through which the bracket can be received, wherein the opening is shaped to allow linear movement of the bracket along the plane as well as rotation of the bracket about an axis that is perpendicular to the plane; and
iv) a fastener that, when engaged, places the bracket system into a locked position, and when disengaged places the bracket system into an unlocked position, wherein the fastener comprises a lever;

wherein the bracket is adapted to be received by the frame, and wherein once the frame is attached to the tooth on a patient and the bracket system is in an unlocked position, the bracket can be rotated about the axis that is perpendicular to the plane, and can be moved into more than one position by moving the bracket linearly along the plane of the receiving member without the frame being removed from or reattached to the tooth.

25. The bracket system of claim 24, wherein the lever has a lever handle and a lever lock, wherein the lever lock, when the lever handle is moved, can lock or unlock the relative positions of the anchoring member and the receiving member.

* * * * *